United States Patent [19]
Ito et al.

[11] Patent Number: 5,807,730
[45] Date of Patent: Sep. 15, 1998

[54] NITRILE HYDRATASE

[75] Inventors: Kiyoshi Ito; Toshifumi Yamaki, both of Mobara; Teruo Arii, Chiba; Miyuki Tsuruoka, Yachimata; Takeshi Nakamura, Ichihara, all of Japan

[73] Assignee: Mitsui Chemicals, Inc., Tokyo, Japan

[21] Appl. No.: 800,751

[22] Filed: Feb. 14, 1997

[30] Foreign Application Priority Data

Feb. 14, 1996 [JP] Japan ................................. 8-027004

[51] Int. Cl.⁶ ................................................. C12N 9/88
[52] U.S. Cl. ................................................. 435/232; 435/822
[58] Field of Search ................................. 435/227, 232, 435/822

[56] References Cited

U.S. PATENT DOCUMENTS 5,314,819  5/1994  Yamada et al. .......................... 435/232

FOREIGN PATENT DOCUMENTS

| | | |
|---|---|---|
| 0445645 | 9/1991 | European Pat. Off. . |
| 56-17918 | 4/1981 | Japan . |
| 59-37951 | 9/1984 | Japan . |
| 62-21519 | 5/1987 | Japan . |
| 62-31914 | 7/1987 | Japan . |
| 2-119778 | 5/1990 | Japan . |
| 3-251184 | 11/1991 | Japan . |
| 4-4873 | 1/1992 | Japan . |
| 4-211379 | 8/1992 | Japan . |
| 6-25296 | 2/1994 | Japan . |
| 6-55148 | 7/1994 | Japan . |
| 6-303971 | 11/1994 | Japan . |

OTHER PUBLICATIONS

Enzymatic synthesis of acrylamide: a success story not yet over (TIBTECH Nov. 1992 [No.10]).

Mayaux et al., "Purification, Cloning, and Primary Structure of a New Enantiomer–Selective Amidase from a Rhodococcus Strain: Structural Evidence for a Conserved Genetic Coupling with Nitrile Hydratase," *Jnl. of Bacteriology*, vol. 173, No. 21, Nov. 1991, pp. 6694–6704.

Yamaki et al., "Cloning and Sequencing of a Nitrile Hydratase Gene from *Pseudonocardia thermophila* JCM3095," *Jnl. of Fermentation and Bioengineering*, vol. 83, No. 5, 1997, pp. 474–477.

J.A. Wells. "Additivity of mutational effects in proteins" Biochemistry 29 (37):8509–8517, Sep. 18, 1990.

Bowie et al. "Deciphering the message in protein sequences: tolerance to amino acid substitutions" Science 247:1306–1310, Mar. 16, 1990.

*Primary Examiner*—Robert A. Wax
*Assistant Examiner*—Gabriele E. Bugaisky
*Attorney, Agent, or Firm*—Burns, Doane, Swecker & Mathis, L.L.P.

[57] ABSTRACT

The present invention provides the amino acid sequence and base sequence of a *Pseudonocardia thermophila*-derived nitrile hydratase, provides further a method for changing its amino acid sequence and base sequence without substantially changing the functions of said nitrile hydratase, and nitrile hydratases having a base sequence and an amino acid sequence as changed on the basis of said method, and provides furthermore a recombinant plasmid having the gene of said nitrile hydratase, a transformant containing said recombinant plasmid, a method of using said transformant for producing said enzyme, and a method of using said transformant for producing the corresponding amide compound from a nitrile compound.

4 Claims, 2 Drawing Sheets

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
      ( A ) LENGTH: 205 amino acids
      ( B ) TYPE: amino acid
      ( C ) STRANDEDNESS: single
      ( D ) TOPOLOGY: linear ( i i ) MOLECULE TYPE: protein ( v i ) ORIGINAL SOURCE:
      ( A ) ORGANISM: Pseudonocardia thermophila
      ( B ) STRAIN: JCM3095

( v i i ) IMMEDIATE SOURCE:
      ( B ) CLONE: pPT-DB1

( i x ) FEATURE:
      ( A ) NAME/KEY: Protein
      ( B ) LOCATION: 1..205
      ( D ) OTHER INFORMATION: /note= "Identification Method: E"

( i x ) FEATURE:

(A) NAME/KEY: Protein
(B) LOCATION: 1..205
(D) OTHER INFORMATION: /note= "nitrile hydratase alpha subunit"

(xi) SEQUENCE DESCRIPTION: SEQ ID NO:1:

| Met | Thr | Glu | Asn | Ile | Leu | Arg | Lys | Ser | Asp | Glu | Glu | Ile | Gln | Lys | Glu |
|---|---|---|---|---|---|---|---|---|---|---|---|---|---|---|---|
| 1 | | | | 5 | | | | | 10 | | | | | 15 | |

| Ile | Thr | Ala | Arg | Val | Lys | Ala | Leu | Glu | Ser | Met | Leu | Ile | Glu | Gln | Gly |
|---|---|---|---|---|---|---|---|---|---|---|---|---|---|---|---|
| | | | 20 | | | | | 25 | | | | | | 30 | |

| Ile | Leu | Thr | Thr | Ser | Met | Ile | Asp | Arg | Met | Ala | Glu | Ile | Tyr | Glu | Asn |
|---|---|---|---|---|---|---|---|---|---|---|---|---|---|---|---|
| | | | 35 | | | | | 40 | | | | | 45 | | |

| Glu | Val | Gly | Pro | His | Leu | Gly | Ala | Lys | Val | Val | Val | Lys | Ala | Trp | Thr |
|---|---|---|---|---|---|---|---|---|---|---|---|---|---|---|---|
| | 50 | | | | | | 55 | | | | | 60 | | | |

| Asp | Pro | Glu | Phe | Lys | Lys | Arg | Leu | Leu | Ala | Asp | Gly | Thr | Glu | Ala | Cys |
|---|---|---|---|---|---|---|---|---|---|---|---|---|---|---|---|
| 65 | | | | | 70 | | | | | 75 | | | | | 80 |

| Lys | Glu | Leu | Gly | Ile | Gly | Gly | Leu | Gln | Gly | Glu | Asp | Met | Met | Trp | Val |
|---|---|---|---|---|---|---|---|---|---|---|---|---|---|---|---|
| | | | | 85 | | | | | 90 | | | | | 95 | |

| Glu | Asn | Thr | Asp | Glu | Val | His | His | Val | Val | Val | Cys | Thr | Leu | Cys | Ser |
|---|---|---|---|---|---|---|---|---|---|---|---|---|---|---|---|
| | | | | 100 | | | | | 105 | | | | | 110 | |

| Cys | Tyr | Pro | Trp | Pro | Val | Leu | Gly | Leu | Pro | Pro | Asn | Trp | Phe | Lys | Glu |
|---|---|---|---|---|---|---|---|---|---|---|---|---|---|---|---|
| | | | 115 | | | | | 120 | | | | | 125 | | |

| Pro | Gln | Tyr | Arg | Ser | Arg | Val | Val | Arg | Glu | Pro | Arg | Gln | Leu | Leu | Lys |
|---|---|---|---|---|---|---|---|---|---|---|---|---|---|---|---|
| | | | 130 | | | | | 135 | | | | | 140 | | |

| Glu | Glu | Phe | Gly | Phe | Glu | Val | Pro | Pro | Ser | Lys | Glu | Ile | Lys | Val | Trp |
|---|---|---|---|---|---|---|---|---|---|---|---|---|---|---|---|
| 145 | | | | | 150 | | | | | 155 | | | | | 160 |

| Asp | Ser | Ser | Ser | Glu | Met | Arg | Phe | Val | Val | Leu | Pro | Gln | Arg | Pro | Ala |
|---|---|---|---|---|---|---|---|---|---|---|---|---|---|---|---|
| | | | | 165 | | | | | 170 | | | | | 175 | |

| Gly | Thr | Asp | Gly | Trp | Ser | Glu | Glu | Glu | Leu | Ala | Thr | Leu | Val | Thr | Arg |
|---|---|---|---|---|---|---|---|---|---|---|---|---|---|---|---|
| | | | 180 | | | | | 185 | | | | | 190 | | |

| Glu | Ser | Met | Ile | Gly | Val | Glu | Pro | Ala | Lys | Ala | Val | Ala | | | |
|---|---|---|---|---|---|---|---|---|---|---|---|---|---|---|---|
| | | | 195 | | | | | 200 | | | | | 205 | | |

(2) INFORMATION FOR SEQ ID NO:2:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Pseudonocardia thermophila
        (B) STRAIN: JCM3095

(vii) IMMEDIATE SOURCE:
        (B) CLONE: pPT-DB1

(ix) FEATURE:
        (A) NAME/KEY: Protein
        (B) LOCATION: 1..233
        (D) OTHER INFORMATION: /note= "Identification Method: E"

(ix) FEATURE:
        (A) NAME/KEY: Protein
        (B) LOCATION: 1..233
        (D) OTHER INFORMATION: /note= "nitrile hydratase beta subunit"

(xi) SEQUENCE DESCRIPTION: SEQ ID NO:2:

| Met | Asn | Gly | Val | Tyr | Asp | Val | Gly | Gly | Thr | Asp | Gly | Leu | Gly | Pro | Ile |
|---|---|---|---|---|---|---|---|---|---|---|---|---|---|---|---|
| 1 | | | | 5 | | | | | 10 | | | | | 15 | |

-continued

```
Asn Arg Pro Ala Asp Glu Pro Val Phe Arg Ala Glu Trp Glu Lys Val
            20              25              30

Ala Phe Ala Met Phe Pro Ala Thr Phe Arg Ala Gly Phe Met Gly Leu
            35              40              45

Asp Glu Phe Arg Phe Gly Ile Glu Gln Met Asn Pro Ala Glu Tyr Leu
            50              55              60

Glu Ser Pro Tyr Tyr Trp His Trp Ile Arg Thr Tyr Ile His His Gly
 65              70              75              80

Val Arg Thr Gly Lys Ile Asp Leu Glu Glu Leu Glu Arg Arg Thr Gln
            85              90              95

Tyr Tyr Arg Glu Asn Pro Asp Ala Pro Leu Pro Glu His Glu Gln Lys
            100             105             110

Pro Glu Leu Ile Glu Phe Val Asn Gln Ala Val Tyr Gly Gly Leu Pro
            115             120             125

Ala Ser Arg Glu Val Asp Arg Pro Pro Lys Phe Lys Glu Gly Asp Val
            130             135             140

Val Arg Phe Ser Thr Ala Ser Pro Lys Gly His Ala Arg Ala Arg
145             150             155             160

Tyr Val Arg Gly Lys Thr Gly Thr Val Val Lys His His Gly Ala Tyr
            165             170             175

Ile Tyr Pro Asp Thr Ala Gly Asn Gly Leu Gly Glu Cys Pro Glu His
            180             185             190

Leu Tyr Thr Val Arg Phe Thr Ala Gln Glu Leu Trp Gly Pro Glu Gly
            195             200             205

Asp Pro Asn Ser Ser Val Tyr Tyr Asp Cys Trp Glu Pro Tyr Ile Glu
            210             215             220

Leu Val Asp Thr Lys Ala Ala Ala Ala
225             230
```

(2) INFORMATION FOR SEQ ID NO:3:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudonocardia thermophila
        (B) STRAIN: JCM3095

(vii) IMMEDIATE SOURCE:
        (B) CLONE: pPT-DB1

(ix) FEATURE:
        (A) NAME/KEY: misc_feature
        (B) LOCATION: 1..618
        (D) OTHER INFORMATION: /note= "Identification Method: E"

(ix) FEATURE:
        (A) NAME/KEY: misc_feature
        (B) LOCATION: 1..618
        (D) OTHER INFORMATION: /note= "nitrile hydratase alpha
                subunit"

(xi) SEQUENCE DESCRIPTION: SEQ ID NO:3:

```
ATGACCGAGA  ACATCCTGCG  CAAGTCGGAC  GAGGAGATCC  AGAAGGAGAT  CACGGCGCGG   60
GTCAAGGCCC  TGGAGTCGAT  GCTCATCGAA  CAGGGCATCC  TCACCACGTC  GATGATCGAC  120
CGGATGGCCG  AGATCTACGA  GAACGAGGTC  GGCCCGCACC  TCGGCGCGAA  GGTCGTCGTG  180
AAGGCCTGGA  CCGACCCGGA  GTTCAAGAAG  CGTCTGCTCG  CCGACGGCAC  CGAGGCCTGC  240
```

```
AAGGAGCTCG  GCATCGGCGG  CCTGCAGGGC  GAGGACATGA  TGTGGGTGGA  GAACACCGAC    300

GAGGTCCACC  ACGTCGTCGT  GTGCACGCTC  TGCTCCTGCT  ACCCGTGGCC  GGTGCTGGGG    360

CTGCCGCCGA  ACTGGTTCAA  GGAGCCGCAG  TACCGCTCCC  GCGTGGTGCG  TGAGCCCGG     420

CAGCTGCTCA  AGGAGGAGTT  CGGCTTCGAG  GTCCCGCCGA  GCAAGGAGAT  CAAGGTCTGG    480

GACTCCAGCT  CCGAGATGCG  CTTCGTCGTC  CTCCCGCAGC  GCCCCGCGGG  CACCGACGGG    540

TGGAGCGAGG  AGGAGCTCGC  CACCCTCGTC  ACCCGCGAGT  CGATGATCGG  CGTCGAACCG    600

GCGAAGGCGG  TCGCGTGA                                                      618
```

( 2 ) INFORMATION FOR SEQ ID NO:4:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pseudonocardia thermophila
        ( B ) STRAIN: JCM3095

( v i i ) IMMEDIATE SOURCE:
        ( B ) CLONE: pPT-DB1

( i x ) FEATURE:
        ( A ) NAME/KEY: misc_feature
        ( B ) LOCATION: 1..702
        ( D ) OTHER INFORMATION: /note= "Identification Method: E."

( i x ) FEATURE:
        ( A ) NAME/KEY: misc_feature
        ( B ) LOCATION: 1..702
        ( D ) OTHER INFORMATION: /note= "nitrile hydratase beta
            subunit"

( x i ) SEQUENCE DESCRIPTION: SEQ ID NO:4:

```
ATGAACGGCG  TGTACGACGT  CGGCGGCACC  GATGGGCTGG  GCCCGATCAA  CCGGCCCGCG     60

GACGAACCGG  TCTTCCGCGC  CGAGTGGGAG  AAGGTCGCGT  TCGCGATGTT  CCCGGCGACG    120

TTCCGGGCCG  GCTTCATGGG  CCTGGACGAG  TTCCGGTTCG  GCATCGAGCA  GATGAACCCG    180

GCCGAGTACC  TCGAGTCGCC  GTACTACTGG  CACTGGATCC  GCACCTACAT  CCACCACGGC    240

GTCCGCACCG  GCAAGATCGA  TCTCGAGGAG  CTGGAGCGCC  GCACGCAGTA  CTACCGGGAG    300

AACCCCGACG  CCCCGCTGCC  CGAGCACGAG  CAGAAGCCGG  AGTTGATCGA  GTTCGTCAAC    360

CAGGCCGTCT  ACGGCGGGCT  GCCCGCAAGC  CGGGAGGTCG  ACCGACGCC   CAAGTTCAAG    420

GAGGGCGACG  TGGTGCGGTT  CTCCACCGCG  AGCCCGAAGG  CCACGCCCG   GCGCGCGCGG    480

TACGTGCGCG  GCAAGACCGG  GACGGTGGTC  AAGCACCACG  GCGCGTACAT  CTACCCGGAC    540

ACCGCCGGCA  ACGGCCTGGG  CGAGTGCCCC  GAGCACCTCT  ACACCGTCCG  CTTCACGGCC    600

CAGGAGCTGT  GGGGGCCGGA  AGGGGACCCG  AACTCCAGCG  TCTACTACGA  CTGCTGGGAG    660

CCCTACATCG  AGCTCGTCGA  CACGAAGGCG  GCCGCGGCAT  GA                        702
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc = "synthetic DNA"

(ix) FEATURE:
    (A) NAME/KEY: misc_feature
    (B) LOCATION: 3..18
    (D) OTHER INFORMATION: /note= "Nucleotides 3, 12, 15, and 18 wherein N = A, C, G, or T."

(xi) SEQUENCE DESCRIPTION: SEQ ID NO:5:

ACNGARAAYA TNYTNMGNAA     20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION: 3..18
        (D) OTHER INFORMATION: /note= "Nucleotides 3, 6, 9, and 18 wherein N = A, C, G, or T."

(xi) SEQUENCE DESCRIPTION: SEQ ID NO:6:

TTNCKNARNA TRTTYTCNGT     20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION: 9..18
        (D) OTHER INFORMATION: /note= "Nucleotides 9, 12, and 18 wherein N = A, C, G, or T."

(xi) SEQUENCE DESCRIPTION: SEQ ID NO:7:

ATGAAYGGNG TNTAYGANGT     20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION: 3..12
        (D) OTHER INFORMATION: /note= "Nucleotides 3, 9, and 12 wherein N = A, C, G, or T."

(xi) SEQUENCE DESCRIPTION: SEQ ID NO:8:

ACNTCRTANA CNCCRTTCAT     20

(2) INFORMATION FOR SEQ ID NO:9:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:9:

AACATCATGC GCAAGTCG                           18

( 2 ) INFORMATION FOR SEQ ID NO:10:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:10:

CAGGAAACAG CTATGAC                            17

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:11:

GGCCAGTGCC TAGCTTACAT                         20

( 2 ) INFORMATION FOR SEQ ID NO:12:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:12:

GTTTTCCCAG TCACGAC                            17

( 2 ) INFORMATION FOR SEQ ID NO:13:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:13:

AACATCACGC GCAAGTCG                           18

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:14:

AACATCGCGC GCAAGTCG 18

( 2 ) INFORMATION FOR SEQ ID NO:15:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:15:

AACATCGTGC GCAAGTCG 18

( 2 ) INFORMATION FOR SEQ ID NO:16:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:16:

ATCACGGTGC GGGTCAAG 18

( 2 ) INFORMATION FOR SEQ ID NO:17:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:17:

ACGTCGTTGA TCGACCGG 18

( 2 ) INFORMATION FOR SEQ ID NO:18:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:18:

GACGGCTCCG AGGCCTGC 18

( 2 ) INFORMATION FOR SEQ ID NO:19:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:19:

CTGCAGGCCG AGGACATG         18

( 2 ) INFORMATION FOR SEQ ID NO:20:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:20:

GACGAGGCCC ACCACGTC         18

( 2 ) INFORMATION FOR SEQ ID NO:21:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:21:

CACGTCATCG TGTGCACG         18

( 2 ) INFORMATION FOR SEQ ID NO:22:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:22:

AACTGGTACA AGGAGCCG         18

( 2 ) INFORMATION FOR SEQ ID NO:23:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:23:

GAGCCGGAGT ACCGCTCC         18

( 2 ) INFORMATION FOR SEQ ID NO:24:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "synthetic DNA"

( x i ) SEQUENCE DESCRIPTION: SEQ ID NO:24:

CGGCAGGTGC TCAAGGAG 18

( 2 ) INFORMATION FOR SEQ ID NO:25:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:25:

AAGGAGGACT TCGGCTTC 18

( 2 ) INFORMATION FOR SEQ ID NO:26:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:26:

GAGCTCACCA CCCTCGTC 18

( 2 ) INFORMATION FOR SEQ ID NO:27:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:27:

CGCGAGTTGA TGATCGGC 18

( 2 ) INFORMATION FOR SEQ ID NO:28:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:28:

GCGAAGGAGG TCGCGTGA 18

( 2 ) INFORMATION FOR SEQ ID NO:29:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:29:

CGGCCCGTGG ACGAACCG 18

( 2 ) INFORMATION FOR SEQ ID NO:30:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:30:

CCCGCGAACG AACCGGTC 18

( 2 ) INFORMATION FOR SEQ ID NO:31:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:31:

CTGCCCGATC ACGAGCAG 18

( 2 ) INFORMATION FOR SEQ ID NO:32:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:32:

CTGCCCCCGC ACGAGCAG 18

( 2 ) INFORMATION FOR SEQ ID NO:33:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:33:

CTGCCCTCGC ACGAGCAG 18

( 2 ) INFORMATION FOR SEQ ID NO:34:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic DNA"

( x i ) SEQUENCE DESCRIPTION: SEQ ID NO:34:

CTGCCCCGGC ACGAGCAG 18

( 2 ) INFORMATION FOR SEQ ID NO:35:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:35:

CTGCCCTGCC ACGAGCAG 18

( 2 ) INFORMATION FOR SEQ ID NO:36:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:36:

CTGCCCCTGC ACGAGCAG 18

( 2 ) INFORMATION FOR SEQ ID NO:37:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:37:

CTGCCCACGC ACGAGCAG 18

( 2 ) INFORMATION FOR SEQ ID NO:38:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:38:

TTCACGGACC AGGAGCTG 18

( 2 ) INFORMATION FOR SEQ ID NO:39:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:39:

TTCACGATCC AGGAGCTG    18

( 2 ) INFORMATION FOR SEQ ID NO:40:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:40:

TTCACGGTCC AGGAGCTG    18

( 2 ) INFORMATION FOR SEQ ID NO:41:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:41:

TTCACGGAGC AGGAGCTG    18

( 2 ) INFORMATION FOR SEQ ID NO:42:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:42:

CCGAACTACA GCGTCTAC    18

NITRILE HYDRATASE

DETAILED DESCRIPTION OF THE INVENTION

1. Technical Filed of the Invention

The present invention relates to a novel amino acid sequence that comprises the α-subunit and the β-subunit of a nitrile hydratase as derived from *Pseudonocardia thermophila* JCM3095 (hereinafter referred to as *Pseudonocardia thermophila*), and to a novel gene sequence that codes for the α-subunit and the β-subunit of said enzyme. Further, it relates to a recombinant plasmid containing said gene, to a transformant strain as transformed with said recombinant plasmid, to a method for producing a nitrile hydratase using said transformant strain, and to a method for processing a nitrile compound with a culture as obtained by cultivating cells of said transformant strain, with the cultivated cells or with a product as obtained by processing the cultivated cells, to produce the corresponding amide compound from said nitrile compound.

2. Prior Art

Regarding the technique of hydrating the nitrile group of a nitrile compound to convert it into an amido group, thereby producing the corresponding amide compound from said nitrile compound, there have heretofore been known chemical methods of heating a nitrile compound in the presence of an acid or alkali or in the presence of a copper catalyst.

On the other hand, recently, an enzyme, nitrile hydratase that has a nitrile-hydrating activity of hydrating a nitrile group to convert it into an amido group has been found, and methods of processing a nitrile compound with said enzyme or cells of microorganisms that contain said enzyme to produce the corresponding amide compound from said nitrile compound have already been disclosed (see Japanese Patent Publication Nos. 56-17918, 62-21519, 62-31914, 59-37951, 4-4873 and 6-55148). It is known that these methods are more advantageous than the conventional chemical methods in that the conversion and the selectivity from nitrile compounds into the corresponding amide compounds are higher in the former than those in the latter.

To produce amide compounds from nitrile compounds with such a nitrile hydratase on an industrial scale, it is important to lower the production costs in producing in said enzyme relative to the production costs in producing amide compounds using said enzyme. More concretely, for this, it is necessary to elevate the production rate for producing an amide compound per a unit cell weight and per a unit time (hereinafter referred to as cell activity). Given the situation, various attempts have been being made to clone said enzyme, nitrile hydratase for the purpose of expressing a large amount of said enzyme through genetic engineering means of using the gene of said enzyme. For example, known are the means of using cells of Corynebacterium (see Japanese Patent Application Laid-Open No. 2-119778), cells of Pseudomonas (see Japanese Patent Application Laid-Open No. 3-251184), cells of *Rhodococcus rhodoclous* (see Japanese Patent Application Laid-Open No. 4-211379), cells of Rhizobium (see Japanese Patent Application Laid-Open No. 6-25296, or cells of Klebsiella (see Japanese Patent Application Laid-Open No. 6-303971). However, for Corynebacterium and *Rhodococcus rhodoclous*, it is reported that the nitrile hydratase activity of the transformants of *Escherichia coli* with any of these is extremely weak (see TIBTECH Vol. 10, pp. 402–408, 1992). Thus, it was not always possible to obtain the intended transformants with high cell activity through such genetic engineering means.

PROBLEMS TO BE SOLVED BY THE INVENTION

We, the present inventors have succeeded in, for the first time, isolating a nitrile hydratase gene from cells of *Pseudonocardia thermophila* JCM3095, which we found having a nitrile hydratase activity, and in clarifying its amino acid sequence and gene sequence, and have also succeeded in the formation of genetic recombinant cells capable of expressing a large amount of said gene. On the basis of these findings, we have completed the present invention.

Specifically, one object of the present invention is to provide the amino acid sequence and the gene sequence of a *Pseudonocardia thermophila*-derived nitrile hydratase. The other objects of the invention are to provide a recombinant plasmid having said gene, a transformant having said plasmid, a method for producing said enzyme using cells of said transformant, and a method of processing a nitrile compound with cells of said transformant to produce the corresponding amide compound from it.

Figure 1:
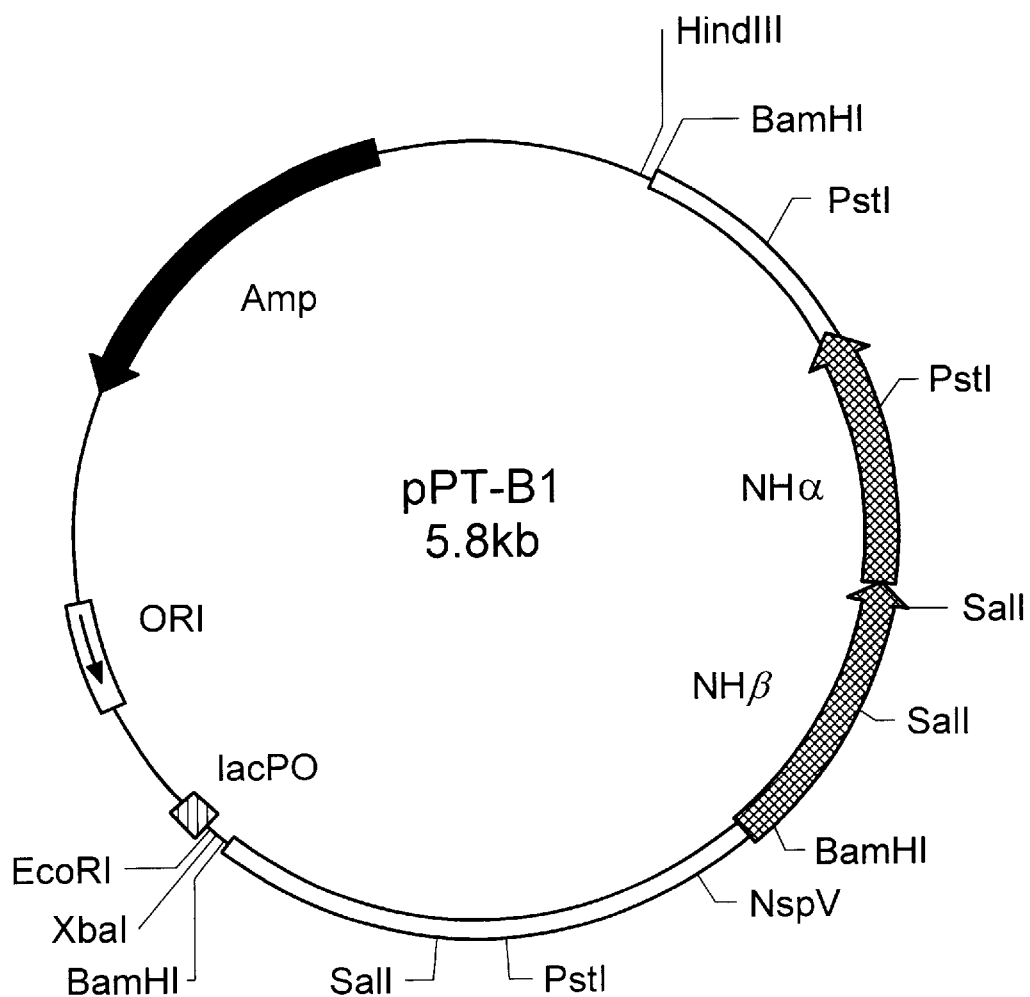
FIG. 1 shows a restriction endonuclease cleavage map of a plasmid pPT-B1.

In these;

Amp indicates a gene coding for β-lactamase,

ORI indicates the replication-starting site in a ColE1 system, lacPO indicates the promoter and operator region in pUC18-derived lactose operon, NHα indicates a gene coding for the α-subunit of *Pseudonocardia thermophila*-derived nitrile hydratase, NHβ indicates a gene coding for the β-subunit of *Pseudonocardia thermophila*-derived nitrile hydratase, and (XbaI/NspV) indicates the site for self-ligation between XbaI and NspV as attained after blunting.

EMBODIMENTS OF CARRYING OUT THE INVENTION

Now, the present invention is described hereinunder. The nitrile hydratase gene of the present invention basically comprises the amino acid sequences of Sequence Number 1 and Sequence Number 2 in Sequence Listing. However, even in transcription and translation from a template of a gene having the same base sequence, one or more amino acids near the N-terminal of an amino acid sequence may be deleted or one or more amino acids may be added to the N-terminal thereof to give mutants having the same enzymatic activity as that of the original, depending on the type of hosts to which the gene is introduced, the components constituting the nutrient medium to be used for incubation of the hosts as well as the composition of the medium, and the temperature and the pH of the medium being used for the incubation, and owing to the modification of the intracellular enzyme after its production through the genetic expression. In addition, with the recent progress in recombinant DNA technology, it has become possible relatively with ease to modify an enzyme, without substantially changing its activity, through substitution, deletion or addition of one or more amino acids in the amino acid sequence of the enzyme. Moreover, recently, various attempts are being made to produce mutant enzymes with improved industrial values, for example, having improved organic solvent resistance or having varied substrate specificity, through substitution, deletion or addition of one or more amino acids in amino acid sequences of enzymes. In view of such technical level in the art, the nitrile hydratase as referred to herein shall include not only those having the amino acid sequences of Sequence Numbers 1 and 2 in Sequence Listing but also any other mutants having amino acid sequences as modified through substitution, deletion or addition of one or more amino acids in said amino acid sequences, provided that they have the intended nitrile hydratase activity, and the present invention shall encompass any and every nitrile hydratase having any of such amino acid sequences and such modified amino acid sequences.

Specifically, the present invention is directed to the nitrile hydratase comprising the α-subunit having the amino acid sequence of 205 amino acids of Sequence Number 1 in Sequence Listing and the β-subunit having the amino acid sequence of 233 amino acids of Sequence Number 2 in Sequence Listing. Needless-to-say, the present invention encompasses any and every nitrile hydratase comprising, as the constitutive element, either one or both of modified α-subunit and β-subunit to be constructed through partial substitution, deletion or addition of one or more amino acids in the amino acid sequences of Sequence Numbers 1 and 2 in Sequence Listing, and having a nitrile-hydrating activity.

In the present invention, the base sequence coding for the α-subunit to be expressed by the amino acid sequence of 205 amino acids of Sequence Number 1 in Sequence Listing is within the scope of the gene coding for the α-subunit constituting the nitrile hydratase of the invention. In addition, provided that any and every protein comprising, as the constitutive element, any modified α-subunit to be constructed through partial substitution, deletion or addition of -one or more amino acids in the amino acid sequence of Sequence Number 1 in Sequence Listing, have a nitrile-hydrating activity, any and every base sequence coding for such a modified α-subunit is within the scope of the nitrile hydratase gene of the present invention. Similarly, in the present invention, the base sequence coding for the β-subunit to be expressed by the amino acid sequence of 233 amino acids of Sequence Number 2 in Sequence Listing is within the scope of the gene coding for the β-subunit constituting the nitrile hydratase of the invention. Also similarly, in addition, provided that any and every protein comprising, as the constitutive element, any modified β-subunit to be constructed through partial substitution, deletion or addition of one or more amino acids in the amino acid sequence of Sequence Number 2 in Sequence Listing, have a nitrile-hydrating activity, any and every base sequence coding for such a modified β-subunit is within the scope of the nitrile hydratase gene of the present invention.

The nitrile hydratase gene of the present invention basically comprises the base sequences of Sequence Numbers 3 and 4 in Sequence Listing. With the recent progress in recombinant DNA technology, however, it has become possible relatively with ease to substitute the base sequence of a DNA to be the template in genetic translation to produce an enzyme, with any other base sequence, without substantially changing the amino acid sequence of said enzyme. In addition, it has become also possible to modify the amino acid sequence of an enzyme into modified ones with substitution, deletion or addition of one or more constitutive amino acids therein, without substantially changing the enzymatic activity of the enzyme, through substitution, deletion or addition in the base sequence of the DNA to be the template in genetic translation to produce the intended enzyme. In view of such technical level in the art, the nitrile hydratase gene as referred to herein shall include not only those having the DNA base sequences of Sequence Numbers 3 and 4 in Sequence Listing but also any other mutants having DNA base sequences as modified through substitution, deletion or addition of one or more bases in said DNA base sequences, provided that they can function as the template for proteins having a nitrile hydratase activity. Specifically, the present invention is directed to the gene coding for a nitrile hydratase, in which the α-subunit comprises the base sequence of 618 bases of Sequence Number 3 in Sequence Listing, while the β-subunit comprises the base sequences of 702 bases of Sequence Number 4 in Sequence Listing. In the present invention, in addition, provided that any and every protein comprising, as the constitutive element, either one or both of the α-subunit of an amino acid sequence which is encoded by any modified base sequence as constructed through partial substitution, deletion or addition in the base sequence of Sequence Number 3 in Sequence Listing, and the β-subunit of an amino acid sequence which is encoded by any modified base sequence as constructed through partial substitution, deletion or addition in the base sequence of Sequence Number 4 in Sequence Listing, have a nitrile-hydrating activity, any and every gene coding for either one or both of such modified α-subunit and β-subunit is within the scope of the nitrile hydratase gene of the present invention.

The present invention further includes the construction of a recombinant plasmid having the nitrile hydratase gene of the invention as inserted thereinto, and the transformation of any desired microorganisms with said recombinant plasmid to give transformants. Moreover, the present invention still includes the production of the intended enzyme through incubation of the resulting transformant cells in ordinary nutrient media, and even the production of amide compounds through contact of said transformant cells, which produce the intended enzyme, with nitrile compounds in aqueous media to convert said nitrile compounds into the corresponding amide compounds.

The recombinant plasmid of the present invention is a plasmid as constructed by inserting the nitrile hydratase gene into a plasmid vector having therein a control region necessary for the expression of said gene and a region necessary for the self-replication thereof, and this can be introduced into any desired host to make it produce the enzyme, nitrile hydratase. As the host employable herein, mentioned is *Escherichia coli,* as in the following examples, which, however, is not limitative. Apart from this, any other microorganisms of the genus Bacillus (such as *Bacillus subtilis*), yeasts, actinomyces and others are also employable. The control region necessary for the expression comprises a promoter sequence (including the operator sequence for control of transcription), a ribosome-binding sequence (SD sequence), and a transcription-terminating sequence. Concretely, the promoter sequence includes a trp promoter of tryptophan operon and a lac promoter of lactose operon that are derived from *Escherichia coli,* a PL promoter and a PR promoter that are derived from lambda phage, and a glucuronic acid synthetase promoter (gnt), an alkali protease promoter (apr), a neutral protease promoter (npr) and an α-amylase promoter (amy) that are derived from *Bacillus subtilis.* In addition to these, also employable herein are a tac promoter and the like that have been modified or designed for themselves. The ribosome-binding sequence includes, for example, those derived from *Escherichia coli* and *Bacillus subtilis,* as well as the sequence intrinsic to *Pseudonocardia thermophila* as in the present invention. Any of these is employable in the present invention with no specific limitation, provided that it functions in desired hosts such as *Escherichia coli* and *Bacillus subtilis*. For example, a consensus sequence comprising a series of 4 or more continuous bases that are complementary to the 3'-terminal region of 16S ribosome RNA may be prepared through DNA synthesis and used herein as the ribosome-binding sequence. The transcription-terminating sequence is not always necessary, for which, however, employable is one not depending on any ρ-factor, for example, a lipoprotein terminator or a trp operon terminator. Regarding the sequence of the control region on the recombinant plasmid, it is desirable that the promoter sequence, the ribosome-binding sequence, the nitrile hydratase gene, and the transcription-terminating sequence are in that order, starting from the upstream side of the 5'-terminal end of the region. In the control region of that type, the α-subunit gene and the β-subunit gene may be expressed for the respective independent cistrons or, alternatively, the two may be expressed together in the polycistronic manner using same control region common to the two.

As examples of the plasmid vector that satisfies the above-mentioned requirements, mentioned are pBR322, pUC18, Bluescript II SK(+), pKK223-3 and pSC101 all having a region self-replicable in *Escherichia coli;* and pUB110, pTZ4, pC194, ρ11, φ1 and φ105 all having a region self-replicable in *Bacillus subtilis.* As examples of the plasmid vector that is self-replicable in two or more different hosts, mentioned are pHV14, TRp7, YEp7 and pBS7.

For the method of inserting the gene that codes for the nitrile hydratase of the invention into the plasmid vector that has the region necessary for the expression of said gene to construct the intended recombinant plasmid of the invention, for the method of transforming a desired host with said recombinant plasmid, and for the method of producing the intended nitrile hydratase of the invention in the cells of the resulting transformant, employable are any ordinary methods and hosts that are generally known in the field of molecular biology, bioengineering and genetic engineering, such as those described in "Molecular Cloning. 2nd Edition" (T. Maniatis et al.; Cold Spring Harbor Laboratory Press, 1988). As the media for incubating transformant cells, generally used are LB medium and M9 medium. More preferably, these medium for use in the present invention comprise Fe ions and Co ions in an amount 0.1 μg/ml or more.

To produce the corresponding amide compound from a nitrile compound by the use of the nitrile hydratase or the transformant cells of the present invention as prepared in the manner mentioned above, a desired nitrile compound is kept in contact with the culture of the transformant cells, or with the transformant cells themselves as isolated from the culture thereof, or with a product as produced by processing the transformant cells, or with a nitrile hydratase as isolated and purified from the transformant cells, in an aqueous medium. The temperature for the contact is not specifically defined, but is preferably within the range within which the nitrile hydratase is not deactivated, more preferably within the range between 0° C. and 50° C. The nitrile compound to be processed is not specifically defined, provided that it may be a substrate on which the nitrile hydratase of the present invention can acts. Preferably, however, it includes, for example, nitrile compounds having from 2 to 4 carbon atoms, such as typically acetonitrile, propionitrile, acrylonitrile, methacrylonitrile, n-butyronitrile, isobutyronitrile, crotononitrile and α-hydroxyisobutyronitrile. The concentration of the nitrile compound in the aqueous medium is not specifically defined at all, provided that it is within the range that does not exceed the degree of maximum solubility of the nitrile compound in said medium. Preferably, however, the nitrile concentration may be 5% by weight or lower, more preferably 2% by weight or lower, in consideration of the activity of the enzyme that may not be deactivated by the nitrile compound.

A series of steps are summarized hereinunder, which we, the present inventors have employed before the clarification of the amino acid sequences and the base sequences of the *Pseudonocardia thermophila*-derived nitrile hydratase of Sequences Numbers 1 to 4 in Sequence Listing. *Pseudonocardia thermophila* JCM3095 has been being stored in Japan Collection of Microorganisms, The Institute of Physical and Chemical Research (RIKEN) of 2-1, Hirosawa, Wako-shi, Saitama-ken, Japan under a code number of JCM3095, which is now available to anyone who requests it.

(1) Cells of the strain are incubated, isolated, disrupted, and subjected to ammonium sulfate fractionation, anion-exchange chromatography, gel filtration chromatography and hydrophobic chromatography to thereby isolate and purify the nitrile hydratase therefrom, of which the amino acid sequences of 7 residues in the N-terminal of the α-subunit and the β-subunit were sequenced.

(2) Based on the thus-sequenced N-terminal amino acid sequences, oligonucleotide primers for genetic amplification were prepared. A chromosome DNA was prepared from the cells. Through PCR using these primers and the chromosome DNA as the template, obtained were amplified DNA products.

(3) The chromosome DNA was partially cleaved with restriction endonucleases to collect DNA fragments of from about 1500 bp to about 4000 bp. Each DNA fragment was linked to a plasmid vector, with which *Escherichia coli* was transformed to give a plasmid library.

(4) Through colony hybridization using, as the probe, the amplified DNA products as obtained in the previous (2), positive clones comprising the DNA fragment that codes for the nitrile hydratase were selected from the plasmid library.

(5) From the positive clones, extracted was the plasmid DNA, and the whole base sequence of the insert fragments was sequenced, whereby the base sequence of the gene that codes for the α-subunit and the β-subunit of the nitrile hydratase was identified. Comparing the amino acid sequences of the α-subunit and the β-subunit that may be presumed from the thus-sequenced base sequence with the N-terminal amino sequences of 7 residues of the both subunits as obtained in the previous (1), it was verified that the base sequence as sequenced previously codes for the nitrile hydratase.

(6) The DNA fragment containing the nitrile hydratase gene was re-prepared from the plasmid of the positive clone, as obtained in the previous (4) and inserted into a plasmid vector having a suitable promoter.

(7) The plasmid as obtained in the pervious (6) was introduced into suitable host cells to obtain transformant cells. These transformant cells were incubated, and isolated from the culture. These cells were then kept into contact with acrylonitrile in an aqueous medium, whereupon the formation of acrylamide was confirmed.

EXAMPLES

Now, the present invention is described in more detail with reference to the following examples, which, however, are not intended to restrict the scope of the invention.

Example 1

Purification of Nitrile Hydratase from *Pseudonocardia thermophila* JCM3095:

Cells of *Pseudonocardia thermophila* JCM3095 were incubated in a nutrient broth medium (pH 7.5) containing 0.2% of methacrylamide, at 50° C. for 3 days. Through centrifugation of the culture (8000×G, 30 minutes) obtained were 3 g of wet cells. These were suspended in 7 g of KPB (0.1M potassium phosphate buffer; pH 7.0), and disrupted using an ultrasonic cell disrupter to give a liquid comprising cell debris. 2.7 g of ammonium sulfate was added to the liquid comprising cell debris, which was gently stirred at 4° C. for 1 hour and then centrifuged (25000×G, 30 minutes) to remove the insoluble solids therefrom. 1.2 g of ammonium sulfate was added to 90 g of the resulting supernatant, which was gently stirred at 4° C. for 1 hour and then centrifuged (25000×G, 30 minutes) to collect the precipitate. The precipitate was dissolved in 1 ml of KPB, and dialyzed against 2 liters of the same KPB at 4° C. for 48 hours. The resulting dialysate was subjected to anion-exchange chromatography using a Toso's DEAE-TOYOPEARL 650M column (column size: 5×6 φcm), from which was obtained a fraction having a nitrile hydratase activity through gradient elution with from 0M to 0.5M potassium chloride, using KPB as the developer. Next, the resulting active fraction was subjected to gel filtration chromatography, using Pharmacia's SUPERDEX200-26/60 as the carrier and using KPB containing 0.2M potassium chloride as the developer, from which was recovered only the fraction having a nitrile hydratase activity. Then, the active fraction was subjected to hydrophobic chromatography using a Toso's TSK Gel Phenyl-5PW column (for HPLC). In this, the active ingredient was adsorbed to the carrier in the column that had been equilibrated with KPB containing ammonium sulfate at a concentration of 20% saturation, and was then eluted through gradient elution with an eluent comprising ammonium sulfate, of which the concentration was decreased from 20% saturation to 0% saturation at a linear gradient, to obtain an active fraction.

In these chromatographic treatments, the nitrile hydratase activity in each fraction was determined in the manner as mentioned below. Each fraction was suitably diluted with KPB, to which was added 1% by weight of acrylonitrile and reacted at 10° C. for 10 minutes. To the reaction mixture, added was an aqueous solution of 1M phosphoric acid, which was the same amount as that of the reaction mixture, to thereby terminate the reaction. Then, the concentration of the thus-formed acrylamide was measured through HPLC analysis. In this, used was ULTRON 80HG (50×8 φmm) as the HPLC column to which was applied a developer of an aqueous solution of 10 mM phosphoric acid. The amount of acrylamide formed was determined through the measurement of the absorbance at 220 nm.

The active fraction as obtained through the hydrophobic chromatography was subjected to SDS-PAGE under a reducing condition, which revealed the presence of two main polypeptide chains of 29K daltons and 32K daltons and three minor polypeptide chains of 45K daltons or higher. SDS-PAGE of ordinary nitrile hydratases under a reducing condition generally gives two polypeptide chains of 30±3K daltons. Each of the two main polypeptide chains of 29K daltons and 32K daltons existing in the SDS-PAGE gel was adsorbed onto a Bio Rad's PVDE membrane, using a Sartorius' semi-dry Electroblotter. From the PVDE membrane, only the part onto which the intended polypeptide chain had been adsorbed was cut out, and the N-terminal amino acid sequence of the polypeptide chain was sequenced using a Shimadzu's peptide sequencer, PSQ-1. As a result, it was found that the N-terminal amino acid sequence of the polypeptide chain of 29K daltons corresponds to from the 2nd to the 8th amino acid residues of the amino acid sequence of Sequence Number 1 in Sequence Listing, and that the N-terminal amino acid sequence of the polypeptide chain of 32K daltons corresponds to from 1st to 7th amino acid residues of the amino acid sequence of Sequence Number 2 in Sequence Listing.

Example 2

Isolation of Nitrile Hydratase Gene from *Pseudonocardia thermophila* JCM3095:

Cells of *Pseudonocardia thermophila* JCM3095 were incubated in the same manner as in Example 1. The culture was centrifuged (8000×G, 30 minutes) to collect 2 g of wet cells therefrom. To these was added 40 ml of an aqueous solution of 50 mM EDTA·2Na (pH 8.0) containing 0.15M NaCl to prepare a cell suspension, which was then boiled at 90° C. for 10 minutes. The resulting suspension was cooled to 37° C., to which was added 100 mg of egg white lysozyme and kept at 37° C. for 1 hour. Next, 30 mg of zymolylase of 20,000 U/mg was added to this, and kept at 37° C. for 1 hour. Subsequently, 5 mg of proteinase K of 20 U/mg was added to this, and kept at 37° C. for 1 hour. Further, 2 ml of 10% SDS solution was added to this and kept at 65° C. for 1 hour, which was then immediately subjected to phenol/chloroform extraction. Precisely, 42 ml of phenol as saturated with TE (10 mM Tris-HCl buffer containing 1 mM EDTA-2Na; pH 8.0) was added to the reaction mixture and then gently stirred. This was centrifuged (3000 rpm, 10 minutes) to separate it into an aqueous phase and an organic phase, and only the aqueous phase was collected. To this aqueous phase, added were 21 ml of the above-mentioned TE-saturated phenol and 21 ml of chloroform, and gently stirred. Then, this was again centrifuged (3000 rpm, 10 minutes) to separate it into an aqueous phase and an organic phase, and only the aqueous phase was collected. To this aqueous phase, added was 42 ml of chloroform, and gently stirred. Then, this was still again centrifuged (3000 rpm, 10 minutes) to separate it into an aqueous phase and an organic phase, and only the aqueous phase was collected. To this aqueous phase, added were 4 ml of TE containing 1.1M NaCl and 92 ml of ethanol, and then left as at room temperature for a while. Then, the yarn-like DNA thus precipitated was collected by winding it around a glass rod. This was dewatered through treatment with aqueous solutions of 70%, 80% and 90% ethanol in that order, and then dried in air. Next, the thus-collected DNA was again dissolved in 40 ml of TE. To this was added 30 μg of RNase A, and kept at 37° C. for 1 hour. Next, this was partially cleaved with a restriction endonuclease BamHI. The DNA thus partially cleaved was again purified through phenol/chloroform extraction followed by ethanol precipitation, and this was dissolved in TE to have a final concentration of 1.0 μg/μl.

On the basis of the N-terminal amino acid sequences of the polypeptide chains of 29K daltons and 32K daltons, that had been sequenced in Example 1, the following four PCR primers were prepared.

Primer 1: 5'-ACNGARAAYATNYTNMGNAA-3'(SEQ ID NO: 5)

Primer 2: 5'-TTNCKNARNATRTTYTCNGT-3'(SEQ ID NO: 6)

Primer 3: 5'-ATGAAYGGNGTNTAYGANGT-3'(SEQ ID NO: 7)

Primer 4: 5'-ACNTCRTANACNCCRTTCAT-3'(SEQ ID NO: 8)

The primer 1 of Sequence Number 5 in Sequence Listing, and the primer 2 of Sequence Number 6 in the same correspond to the respective complementary chains of the DNA chain that reversely corresponds to the N-terminal amino acid sequence of the polypeptide chain of 29K daltons. The primer 3 of Sequence Number 7 in Sequence Listing, and the primer 4 of Sequence Number 8 in the same correspond to the respective complementary chains of the DNA chain that reversely corresponds to the N-terminal amino acid sequence of the polypeptide chain of 32K daltons. In these, N indicates A, C, G or T.

3 μg of the chromosome DNA that had been partially cleaved hereinabove was subjected to PCR, using it as the template. Precisely, for PCR reaction No. 1, used was a reaction system of 100 μl in total, comprising 3 μg of the DNA, 200 ng of the primer 1,200 ng of the primer 4 and 5 U of Taq DNA polymerase. The reaction No. 1 was comprised of 40 PCR cycles, in which one PCR cycle comprised thermal denaturation at 94° C. for 1 minute, annealing at 37° C. for 1 minute and chain extension at 72° C. for one minute. For PCR reaction No. 2, used was a reaction system of 100 μl in total, comprising 3 μg of the DNA, 200 ng of the primer 2, 200 ng of the primer 3 and 5 U of Taq DNA polymerase. The reaction No. 2 was comprised of 40 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the presence of the amplified DNA product of about 700 bp only in the reaction mixture obtained in the PCR reaction No. 2. This verified that, in *Pseudonocardia thermophila*, a gene of 32K daltons and a gene of 29K daltons exist while being adjacent to each other in that order from the upstream region of the 5'-terminal side of the combination of these genes.

A solution of the chromosome DNA that had been partially cleaved with BamHI hereinabove was subjected to agarose gel electrophoresis (using a low-melting-point agarose, Sigma's Type VII, at an agarose concentration of 0.6% by weight), and an agarose fragment comprising a DNA fragment of from about 1500 bp to about 4000 bp was cut out of the agarose gel. This agarose fragment (about 0.5 g) was finely pulverized, suspended in 5 ml of TE, and heated at 55° C. for 1 hour, whereby the fragment was completely melted in TE. The resulting agarose melt was subjected to the same phenol/chloroform extraction and ethanol precipitation as in the above, thereby purifying the DNA fragment. The thus-purified DNA fragment was prepared in that manner in an amount of at lest 10 pmol, and inserted into the BamHI site existing in the multi-cloning site of a plasmid vector pUC18 (produced by Takara Shuzo), using a Takara Shuzo's DNA ligation kit. Prior to being used in this ligation, the pUC18 plasmid vector DNA was cleaved with a restriction endonuclease BamHI, then purified through phenol/chloroform extraction and ethanol precipitation, subjected to dephosphorylation of the 5'-terminal thereof with an alkali phosphatase (produced by Takara Shuzo), and again purified through phenol/chloroform extraction and ethanol precipitation. 20 ng of the pUC plasmid vector DNA that had been processed and purified in that manner was used in the ligation.

With the thus-ligated DNA, competent cells of *Escherichia coli* HB101 (COMPETENT HIGH, produced by Toyobo Co., Ltd.) were transformed. About 10 μl of the liquid comprising the thus-transformed cells was applied onto an LB agar medium dishes (0.5 wt. % Bacto yeast-extract, 1 wt. % Bacto trypton, 0.5 wt. % sodium chloride, 1.5 wt. % agar; pH 7.5) containing 50 μg/ml of ampicillin and they were incubated at 37° C. overnight. Thus were obtained a number of laboratory dishes each containing the medium that had from 100 to 1000 colonies/dish appeared thereon.

The plasmid library comprising the chromosome DNA was subjected to colony hybridization using, as the probe, the PCR-amplified DNA product that had been prepared hereinabove, and thus screened to select the clones comprising the intended nitrile hydratase gene.

Precisely, a nylon membrane, Amersham's Hybond-N was gently put onto each dish of the plasmid library, and after about one minute, this was gently peeled off. The thus-peeled membrane was then dipped in a denaturation liquid (aqueous solution of 0.5M NaOH containing 1.5M NaCl) for 7 minutes, and then processed with a neutralization liquid (an aqueous solution of 0.5M Tris-HCl containing 1.5M NaCl and 1 mM EDTA-2Na; pH 7.2) for 3 minutes. This neutralization was repeated twice. Next, this was washed once with 2×SSC (1×SSC is an aqueous solution of one liter comprising 8.76 g of sodium chloride and 4.41 g of sodium citrate), and then put on dry filter paper, on which the membrane was dried in air. The membrane was then exposed to UV at 120 mJ/cm$^2$, by which the DNA was fixed onto the membrane. The thus-processed membranes were subjected to prehybridization, by dipping them in 30 ml/membrane of a hybridization buffer (5×SSC further containing 1 wt. % skim milk, 0.1 wt. % N-lauroylsarcosine, 0.02 wt. % SDS, and 50 wt. % formamide) for 2 hours at 42° C. On the other hand, using the PCR-amplified DNA product that had been prepared hereinabove, as the template, and using a Boehringer Mannheim's DIG-DNA labeling kit, a fluorescence-labeled probe was prepared. 100 ng of the fluorescence-labeled probe and 300 ng of the pUC18 plasmid DNA were, after having been thermally denatured through boiling at 95° C. for 10 minutes, transferred into 10 ml of the hybridization buffer along with the prehybridized membrane. After these were hybridized at 42° C. for 24 hours therein, the membrane was washed twice with 150 ml of 2×SSC containing 0.1 wt. % SDS, at room temperature. Next, this was again washed twice with 150 ml of 1×SSC containing 0.1 wt. % SDS, at 68° C. for 5 minutes. This was further washed with 100 ml of a buffer A (0.1M maleic acid buffer containing 0.3 wt. % Tween 20 and 0.15M NaCl; pH 7.5) for 5 minutes, and then blocked in a buffer B (0.1M maleic acid buffer containing 0.3 wt. % Tween 20, 0.15M NaCl and 1 wt. % skim milk; pH 7.5) at room temperature for 30 minutes. Next, this was washed twice with 300 ml of the buffer A at room temperature for 15 minutes, and then equilibrated in 60 ml of a buffer C (aqueous solution of 0.1M Tris-HCl containing 0.1M NaCl and 50 mM magnesium chloride; pH 9.5) for 5 minutes. This membrane was then dipped in 30 ml of a solution that had been prepared by diluting a luminescent substrate, Boehringer Mannheim's AMPPD 100-fold with the buffer C, at room temperature for 10 minutes, and transferred onto dry filter paper, which absorbed the excess AMPPD. The membrane thus processed according to the process mentioned hereinabove was wrapped with a polyethylene film, which was then subjected to X-ray photography. On the resulting X-ray film, the position of the fluorescent signal appeared was confirmed. This verified the presence of one positive signal on the membrane, and the positive colony from which the membrane had been prepared was confirmed on the original laboratory dish.

The thus-confirmed positive colony was transplanted from the dish onto 10 ml of a liquid LB medium containing ampicillin, and incubated therein overnight at 37° C. with stirring at 250 rpm. The plasmid DNA was extracted from the thus-incubated cells in an ordinary manner, then cleaved with a restriction endonuclease BamHI, and thereafter subjected to agarose gel electrophoresis (where the agarose concentration was 0.7% by weight) to thereby determine the size of the insert fragment, resulting in that the size thereof was about 3.1 Kbp. This plasmid is referred to as pPT-Bl (see FIG. 1). The full-length base sequence of the insert fragment was sequenced according to the primer extension method using ABI's sequencing kit and autosequencer 373A. As a result, it was verified that the insert fragment comprised open reading frames, one having a base sequence of 702 bp and the other having a base sequence of 618 bp, as bonded to each other in that order from the 5'-terminal side thereof. These open reading frames are referred to as ORF1 and ORF2. The four bases constituting the most 3'-terminal side of the ORF1 including the translation terminating codon, over lapped with the four bases constituting the most 5'-terminal side of ORF2, which thus well corresponded to the result obtained through PCR. In addition, the amino acid sequence of the N-terminal side composed of seven amino acid residues, which had been presumed from the base sequence of ORF1, was completely the same as the amino acid sequence of the N-terminal side of the polypeptide chain of 32K daltons that had been obtained in Example 1. This sequence region corresponds to the sequence of from the 1st to the 7th amino acid residues of the amino acid sequence of Sequence Number 2 in Sequence Listing. On the other hand, the amino acid sequence of from the 2nd to the 8th N-terminal side composed of seven amino acid residues, which had been presumed from the base sequence of ORF2, was completely the same as the amino acid sequence of the N-terminal side of 7 amino acid residues of the polypeptide chain of 29K daltons that had been obtained in Example 1. This sequence region corresponds to the sequence of from the 2nd to the 8th amino acid residues of the amino acid sequence of Sequence Number 1 in Sequence Listing. In addition, high homology was admitted between the amino acid sequences of ORF1 and ORF2, and those of the β-subunit and α-subunit, respectively, of a different nitrile hydratase. From these, it was confirmed that the ORF1 is the β-subunit gene of the *Pseudonocardia thermophila*-derived nitrile hydratase and that the ORF2 is the α-subunit gene of the same.

Example 3

Figure 2:
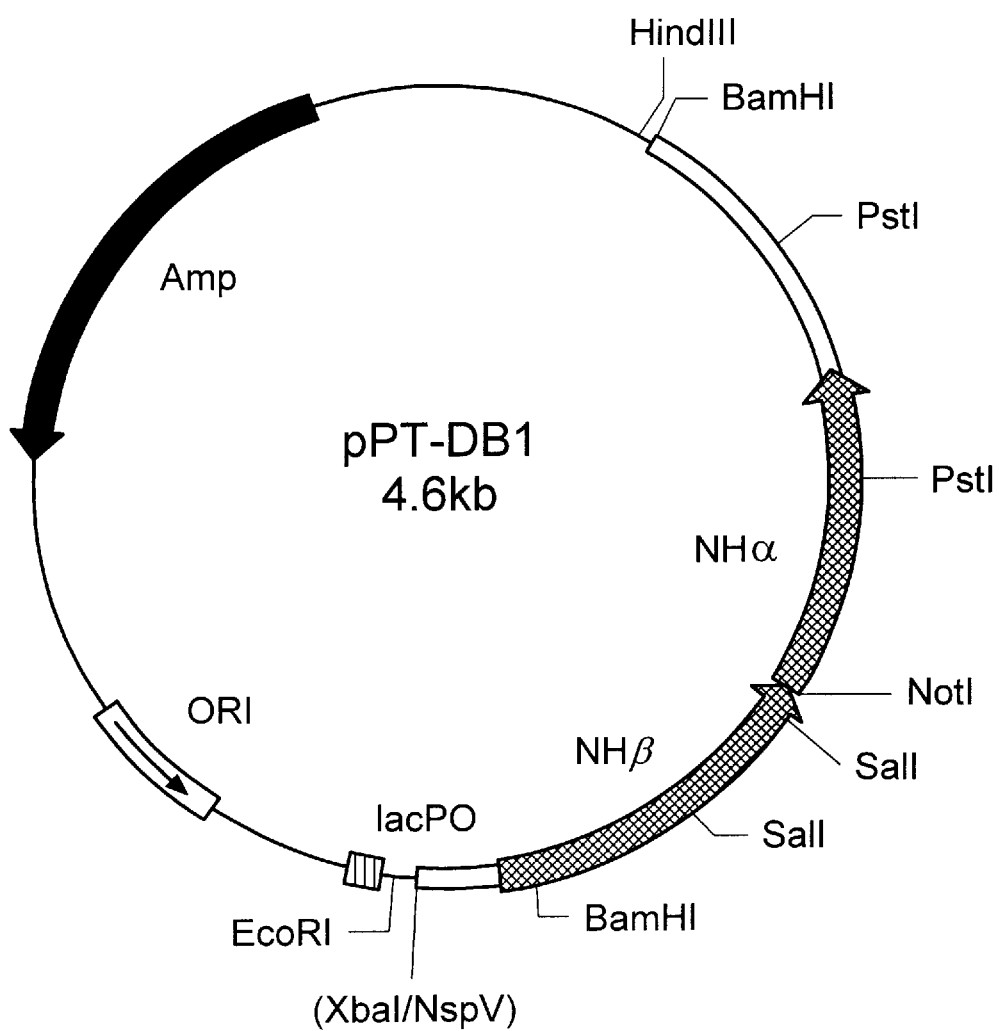
FIG. 2 shows a restriction endonuclease cleavage map of a plasmid pPT-DB1.

Construction of Transformant:

The transcription direction of the lac promoter on the pPT-B1 was completely the same as that of the ORF1 and that of the ORF2. The pPT-B1 was cleaved with restriction endonucleases XbaI and NspV at its sites capable of being cleaved with these restriction endonucleases, these sites existing in the upstream region of the 5'-terminal side of the nitrile hydratase gene of the pPT-B1 and the pPT-B1 being able to be cleaved only at these sites, and then subjected to agarose gel electrophoresis (using a low-melting-point agarose, Sigma's Type VII, at an agarose concentration of 0.7%), through which only the DNA fragment of about 4.6 Kbp was cut out of the plasmid. The thus-cut agarose fragment (about 0.1 g) was finely pulverized, suspended in 1 ml of TE, and then heated at 55° C. for 1 hour to thereby completely melt the agarose fragment. The resulting melt was subjected to the same phenol/chloroform extraction and ethanol precipitation as in Example 2, through which the DNA fragment was purified. This was blunted, using a Takara Shuzo's DNA blunting kit, and then self-ligated using a Takara Shuzo's DNA ligation kit to thereby construct a plasmid pPT-DB1 (FIG. 2). This pPT-DB1 was introduced into competent cells of *Escherichia coli* HB101 (produced by Toyobo Co., Ltd.) whereby HB101 was transformed into a transformant MT-10822. In the transformant MT-10822, the nitrile hydratase gene was transcribed and translated via the lac promoter on the pUC18 existing therein. The transformant MT-10822 was deposited on Feb. 7, 1996 and assigned deposit No. FERM P-15426 in National Institute of Bioscience and Human-Technology, Agency of Industrial Science and Technology, Ministry of International Trade and Industry of 1-3, Higashi 1 chome, Tsukuba-shi, Ibaraki-ken, 305, Japan, and transferred to deposit under the Budapest Treaty on Jan. 10, 1997 and assigned deposit No. FERM BP-5785 in said depository.

Example 4

Conversion (1) of Nitrile Compound into Amide Compound with Transformant:

100 ml of a liquid LB medium comprising 40 μg/ml of ferric sulfate 7-hydrate and 10 μg/ml of cobalt chloride dihydrate was put into a 500-ml Erlenmeyer flask equipped with baffles, and sterilized by autoclaving it at 121° C. for 20 minutes. Ampicillin was added to this medium to have a final concentration of 100 μg/ml. Then, one platinum loop of the cells of MT-10822 that had been prepared in Example 3 were inoculated on the medium, and incubated therein at 37° C. for about 20 hours with stirring at 130 rpm. The resulting culture was centrifuged (5000 G×15 minutes) to separate only the cells therefrom, and the cells were suspended in 50 ml of a physiological saline solution. The resulting suspension was again centrifuged to separate the wet cells therefrom. 100 mg of the wet cells were suspended in 200 ml of an aqueous solution of 50 mM potassium phosphate (pH 7.0), to which was added 10 ml of acrylonitrile and reacted for 1 hour while gently stirring at 10° C. After the reaction, the reaction mixture was subjected to the same HPLC analysis as in Example 1, which verified the presence of only acrylamide in the reaction mixture and the absence of acrylonitrile and acrylic acid therein. Thus, the degree of conversion and the degree of selectivity in this reaction were 100%.

Example 5

Conversion (2) of Nitrile Compound into Amide Compound with Transformant:

100 ml of a liquid LB medium comprising 40 μg/ml of ferric sulfate 7-hydrate and 10 μg/ml of cobalt chloride dihydrate was put into a 500-ml Erlenmeyer flask equipped with baffles, and sterilized by autoclaving it at 121° C. for 20 minutes. Ampicillin was added to this medium to have a final concentration of 100 μg/ml. Then, one platinum loop of the cells of MT-10822 that had been prepared in Example 3 were inoculated on the medium, and incubated therein at 37° C. for about 20 hours with stirring at 130 rpm. The resulting culture was centrifuged (5000 G×15 minutes) to separate only the cells therefrom. The cells were suspended in 50 ml of a physiological saline solution. The resulting suspension was again centrifuged to separate the wet cells therefrom. 100 mg of the wet cells were suspended in 200 ml of an aqueous solution of 50 mM potassium phosphate (pH 7.0), to which was added 50 ml of methacrylonitrile and reacted for 2 hours with gently stirring at 10° C. After the reaction, the reaction mixture was subjected to the same HPLC analysis as in Example 1, which verified the presence of only methacrylamide in the reaction mixture and the absence of methacrylonitrile and methacrylic acid therein. Thus, the degree of conversion and the degree of selectivity in this reaction were 100%.

Example 6

The Mutant (1) with the Partial Substituted Amino Acid Sequence Having Nitrile Hydratase Activity:

This is to demonstrate the substitution with Met for the 6th Leu in the α-subunit region in the plasmid DNA pPT-DB1 that had been prepared in Example 3. Using it as the template, the plasmid DNA pPT-DB1 was subjected to site-specific mutation using a Takara Shuzo's "LA PCR in vitro mutagenesis Kit", in the manner mentioned below. The "LA PCR in vitro mutagenesis Kit" is hereinunder referred to as the kit. In the process for the mutation mentioned below, the kit was handled on the basis of the principle thereof and in accordance with the manufacturer's instructions for the kit.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the cells of MT-10822 that had been prepared in Example 3 were inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA pPT-DB1 through alkali SDS extraction.

One μg of the plasmid DNA pPT-DB1 was subjected to PCR of two different types, using it as the template. Precisely, for PCR reaction No. 1, used was a reaction system of 50 μl in total, comprising 50 pmols of the primer having the sequence of Sequence Number 9 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. From these PCR reaction mixtures, removed were the excess primers and DNTP, using Takara Shuzo 's Microcon 100. To each was added TE to prepare TE solutions of 50 μl each. Annealing solution of 47.5 μl in total was prepared, containing 0.5 μ of both of the above TE solutions. For the basic composition of the annealing solution, referred to were the manufacturer's instructions for the kit. This solution was then thermally denatured at 98° C. for 10 minutes, then cooled to 37° C. at a constant cooling rate over a period of 60 minutes, and thereafter kept at 37° C. for 15 minutes. Thus, the intended annealing was finished. 0.5 μl of TAKARA LA Taq was added to the thus-annealed solution, and then heated at 72° C. for 3 minutes. Thus, the formation of heterologous double-stranded DNA was completed, which was then subjected to PCR reaction No. 3. Precisely, for the PCR reaction No. 3, used was a reaction system of 50 μl in total, comprising 48 μl of said heterologus double-stranded DNA solution,50 pmols of an M13 primer M4 (having the sequence of Sequence Number 10 in Sequence Listing) and 50 pmols of an M13 primer RV (having the sequence of Sequence Number 12 in Sequence Listing). The PCR reaction No. 3 was comprised of 25 PCR cycles, in which one PCR cycle comprised thermal denaturation at 98° C. for 15 seconds, annealing at 55° C. for 30 seconds and chain extension at 72° C. for 120 seconds. After PCR, 5 μl of the reaction mixture obtained in the PCR reaction No. 3 was subjected to agarose gel electrophoresis (using a low-melting-point agarose, Sigma's Type VII at an agarose concentration of 0.8% by weight), thereby detecting the product resulting from the amplification of the DNA in the reaction mixture. This detection revealed the production of the amplified DNA product of about 2.0 Kbp in the PCR reaction No. 3. From the PCR reaction mixture, taken out was only the DNA fragment of about 2.0 Kbp. This fragment (about 0.1 g) was finely pulverized, suspended in 1 ml of TE, and heated at 55° C. for 1 hour, whereby the fragment was completely melted. The resulting melt was then subjected to the same phenol/chloroform extraction and ethanol precipitation as in Example 2, through which the DNA fragment was purified. Finally, this was dissolved in 10 μl of TE. The amplified DNA fragment of about 20 Kbp thus purifiedwas cleavedwith restriction endonucleases EcoRI and HindIII, and then subjected to the same phenol/chloroform extraction and ethanol precipitation as in Example2, through which the DNA fragment was purified. Finally, this was dissolved in 10 μl of TE. On the other hand, the plasmid pPT-DB1 was cleaved with restriction endonucleases EcoRI and HindIII at their cleaving sites, then subjected to agarose gel electrophoresis (using a low-melting-point agarose, Sigma's Type VII, at an agarose concentration of 0.7%), through which only the DNA fragment of about 2.7 Kbp was cut out of the agarose gel. The thus-cut agarose fragment (about 0.1 g) was finely pulverized, suspended in 1 ml of TE, and heated at 55° C. for 1 hour, whereby the fragment was completely melted in TE. The resulting melt was subjected to the same phenol/chloroform extraction and ethanol precipitation as in Example 2, through which the DNA fragment was purified. Finally, this was dissolved in 10 μl of TE. The amplified DNA product and the pPT-DB1 fragment thus prepared in the above were ligated together, using a Takara Shuzo's DNA ligation kit, with which competent cells of *Escherichia coli* HB101 (produced by Toyobo) was transformed. Thus was prepared an *E. coli* bank.

10 ml of a liquid LB medium comprising 40 μg/ml of ferric sulfate 7-hydrate and 10 μg/ml of cobalt chloride dihydrate (this medium is hereinafter referred to as an activity expressionmedium) was put into a 30-ml test tube, and sterilized by autoclaving it at 121° C. for 20minutes. Ampicillin was added to this medium to have a final concentration of 100 μg/ml. Then, one platinum loop of any one of five clones as unlimitedly selected from the *E. coli* bank was inoculated on the medium, and incubated therein at 37° C. for about 20 hours with stirring at 300 rpm. One ml of the resulting culture was put into a suitable centrifugal tube and centrifuged (at 15,000 rpm for 15 minutes) to thereby separate the cells from the culture. The cells were suspended in 200 µl of a potassium phosphate buffer (pH 7.0), to which was added 1% by weight of acrylonitrile and reacted at 10° C. for 2 minutes. To the reaction mixture, added was the same amount, as that of the reaction mixture, of an aqueous solution of 1M phosphoric acid, with which the reaction was terminated. The concentration of the acrylamide thus produced in the reaction mixture was determined through the same HPLC analysis as in Example 1. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced through the same primer extension as in Example 2, using the same ABI's sequencing kit and auto-sequencer 373A. The results are shown in Table 1, in which it is known that the 6th Leu in the α-subunit of the nitrile hydratase from the clone shown therein was substituted with Met.

TABLE 1

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 1 | 6th position in α-subunit | Leu | Met | CTG | ATG |

Example 7

The Mutant (2) with the Partial Substituted Amino Acid Sequence Having Nitrile Hydratase Activity:

This is to demonstrate the substitution with Thr for the 6th Leu in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 13 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 2, in which it is known that the 6th Leu in the α-subunit of the nitrile hydratase from the clone shown therein was substituted with Thr.

TABLE 2

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 2 | 6th position in α-subunit | Leu | Thr | CTG | ACG |

Example 8

The Mutant (3) with the Partial Substituted Amino Acid Sequence Having Nitrile Hydratase Activity:

This is to demonstrate the substitution with Ala for the 6th Leu in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 14 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 3, in which it is known that the 6th Leu in the α-subunit of the nitrile hydratase from the clone shown therein was substituted with Ala.

TABLE 3

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 3 | 6th position in α-subunit | Leu | Ala | CTG | GCG |

Example 9

The Mutant (4) with the Partial Substituted Amino Acid Sequence Having Nitrile Hydratase Activity:

This is to demonstrate the substitution with Val for the 6th Leu in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50 µl in total, comprising 50 pmols of the primer having the sequence of Sequence Number 15 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 4, in which it is known that the 6th Leu in the α-subunit of the nitrile hydratase from the clone shown therein was substituted with Val.

TABLE 4

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 4 | 6th position in α-subunit | Leu | Val | CTG | GTG |

Example 10

The Mutant (5) with the Partial Substituted Amino Acid Sequence Having Nitrile Hydratase Activity:

This is to demonstrate the substitution with Val for the 19th Ala in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50µl in total, comprising 50 pmols of the primer having the sequence of Sequence Number 16 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 5, in which it is known that the 19th Ala in the α-subunit of the nitrile hydratase from the clone shown therein was substituted with Val.

TABLE 5

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 5 | 19th position in α-subunit | Ala | Val | GCG | GTG |

Example 11

The Mutant (6) with the Partial Substituted Amino Acid Sequence Having Nitrile Hydratase Activity:

This is to demonstrate the substitution with Leu for the 38th Met in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50 µl in total, comprising 50 pmols of the primer having the sequence of Sequence Number 17 in Sequence Listing and 50 pmols of an M13 primer M4 (having the sequence of Sequence Number 10 in Sequence Listing) (for the composition of this system, referred to were themanufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 6, in which it is known that the 38th Met in the α-subunit of the nitrile hydratase from the clone shown therein was substituted with Leu.

TABLE 6

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 6 | 38th position in α-subunit | Met | Leu | ATG | TTG |

Example 12

The Mutant (7) with the Partial Substituted Amino Acid Sequence Having Nitrile Hydratase Activity:

This is to demonstrate the substitution with Ser for the 77th Thr in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 18 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 7, in which it is known that the 77th Thr in the α-subunit of the nitrile hydratase from the clone shown therein was substituted with Ser.

TABLE 7

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 7 | 77th position in α-subunit | Thr | Ser | ACC | TCC |

Example 13

The Mutant (8) with the Partial Substituted Amino Acid Sequence Having Nitrile Hydratase Activity:

This is to demonstrate the substitution with Ala for the 90th Gly in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 19 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 11 of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 8, in which it is known that the 90th Gly in the α-subunit of the nitrile hydratase from the clone shown therein was substituted with Ala.

TABLE 8

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 8 | 90th position in α-subunit | Gly | Ala | GGC | GCC |

Example 14

The Mutant (9) with the Partial Substituted Amino Acid Sequence Having Nitrile Hydratase Activity:

This is to demonstrate the substitution with Ala for the 102nd Val in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 20 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 9, in which it is known that the 102nd Val in the α-subunit of the nitrile hydratase from the clone shown therein was substituted with Ala.

TABLE 9

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 9 | 102nd position in α-subunit | Gly | Ala | GTC | GCC |

Example 15

The Mutant (10) with the Partial Substituted Amino Acid Sequence Having Nitrile Hydratase Activity:

This is to demonstrate the substitution with Ile for the 106th Val in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 21 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 10, in which it is known that the 106th Val in the α-subunit of the nitrile hydratase from the clone shown therein was substituted with Ile.

TABLE 10

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 10 | 106th position in α-subunit | Val | Ile | GTC | ATC |

Example 16

The Mutant (11) with the Partial Substituted Amino Acid Sequence Having Nitrile Hydratase Activity:

This is to demonstrate the substitution with Tyr for the 126th Phe in the (α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 22 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 11, in which it is known that the 126th Phe in the α-subunit of the nitrile hydratase from the clone shown therein was substituted with Tyr.

TABLE 11

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 11 | 126th position in α-subunit | Phe | Tyr | TTC | TAC |

Example 17

The Mutant (12) with the Partial Substituted Amino Acid Sequence Having Nitrile Hydratase Activity:

This is to demonstrate the substitution with Glu for the 130th Gln in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50 μl in total, comprising 50 pmols of the primer having the sequence of Sequence Number 23 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 12, in which it is known that the 130th Gln in the α-subunit of the nitrile hydratase from the clone shown therein was substituted with Glu.

TABLE 12

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 12 | 130th position in α-subunit | Gln | Glu | CAG | GAG |

Example 18

The Mutant (13) with the Partial Substituted Amino Acid Sequence Having Nitrile Hydratase Activity:

This is to demonstrate the substitution with Val for the 142nd Leu in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50 µl in total, comprising 50 pmols of the primer having the sequence of Sequence Number 24 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 13, in which it is known that the 142nd Leu in the α-subunit of the nitrile hydratase from the clone shown therein was substituted with Val.

TABLE 13

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 13 | 142nd position in α-subunit | Leu | Val | CTG | GTG |

Example 19

The Mutant (14) with the Partial Substituted Amino Acid Sequence Having Nitrile Hydratase Activity:

This is to demonstrate the substitution with Asp for the 146th Glu in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50 µl in total, comprising 50 pmols of the primer having the sequence of Sequence Number 25 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 14, in which it is known that the 146th Glu in the α-subunit of the nitrile hydratase from the clone shown therein was substituted with Asp.

TABLE 14

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 14 | 146th position in α-subunit | Glu | Asp | GAG | GAC |

Example 20

The Mutant (15) with the Partial Substituted Amino Acid Sequence Having Nitrile Hydratase Activity:

This is to demonstrate the substitution with Thr for the 187th Ala in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50μl in total, comprising 50 pmols of the primer having the sequence of Sequence Number 26 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 15, in which it is known that the 187th Ala in the α-subunit of the nitrile hydratase from the clone shown therein was substituted with Thr.

TABLE 15

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 15 | 187th position in α-subunit | Ala | Thr | GCC | ACC |

Example 21

The Mutant (16) with the Partial Substituted Amino Acid Sequence Having Nitrile Hydratase Activity:

This is to demonstrate the substitution with Leu for the 194th Ser in the α-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 27 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the ptasmid DNA of each clone. Next, the base sequence of the nitrile hydratase structural gene of each clone was sequenced in the same manner as in Example 2. The results are shown in Table 16, in which it is known that the 194th Ser in the α-subunit of the nitrile hydratase from the clone shown therein was substituted with Leu.

TABLE 16

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 16 | 194th position in α-subunit | Ser | Leu | TCG | TTG |

Example 22

The Mutant (17) with the Partial Substituted Amino Acid Sequence Having Nitrile Hydratase Activity:

This is to demonstrate the substitution with Glu for the 203rd Ala in the α-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 28 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 17, in which it is known that the 203rd Ala in the α-subunit of the nitrile hydratase from the clone shown therein was substituted with Glu.

TABLE 17

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 17 | 203rd position in α-subunit | Ala | Glu | GCG | GAG |

Example 23

The Mutant (18) with the Partial Substituted Amino Acid Sequence Having Nitrile Hydratase Activity:

This is to demonstrate the substitution with Val for the 20th Ala in the β-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 29 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 18, in which it is known that the 20th Ala in the β-subunit of the nitrile hydratase from the clone shown therein was substituted with Val.

TABLE 18

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 18 | 20th position in β-subunit | Ala | Val | GCG | GTG |

Example 24

The Mutant (19) with the Partial Substituted Amino Acid Sequence Having Nitrile Hydratase Activity:

This is to demonstrate the substitution with Asn for the 21st Asp in the β-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6 was subjected to PCR of two different types, using it as the template. Precisely, for PCR reaction No. 1, used was a reaction system of 50 µl in total, comprising 50 pmols of the primer having the sequence of Sequence Number 30 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 19, in which it is known that the 21st Asp in the β-subunit of the nitrile hydratase from the clone shown therein was substituted with Asn.

TABLE 19

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 19 | 21st position in β-subunit | Asp | Asn | GAC | AAC |

Example 25

The Mutant (20) with the Partial Substituted Amino Acid Sequence Having Nitrile Hydratase Activity:

This is to demonstrate the substitution with Asp for the 108th Glu in the β-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 31 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. Asa result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 20, in which it is known that the 108th Glu in the β-subunit of the nitrile hydratase from the clone shown therein was substituted with Asp.

TABLE 20

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 20 | 108th position in β-subunit | Glu | Asp | GAG | GAT |

Example 26

The Mutant (21) with the Partial Substituted Amino Acid Sequence Having Nitrile Hydratase Activity:

This is to demonstrate the substitution with Pro for the 108th Glu in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 32 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 21, in which it is known that the 108th Glu in the β-subunit of the nitrile hydratase from the clone shown therein was substituted with Pro.

TABLE 21

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 21 | 108th position in β-subunit | Glu | Pro | GAG | CCG |

Example 27

The Mutant (22) with the Partial Substituted Amino Acid Sequence Having Nitrile Hydratase Activity:

This is to demonstrate the substitution with Ser for the 108th Glu in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 33 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 11 of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 22, in which it is known that the 108th Glu in the β-subunit of the nitrile hydratase from the clone shown therein was substituted with Ser.

TABLE 22

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 22 | 108th position in β-subunit | Glu | Ser | GAG | TCG |

Example 28

The Mutant (23) with the Partial Substituted Amino Acid Sequence Having Nitrile Hydratase Activity:

This is to demonstrate the substitution with Arg for the 108th Glu in the β-subunit region in the plasmid DNA pPT-DB1. Using it as the template, the plasmid DNA pPT-DB1 was subjected to site-specific mutation in the same manner as in Example 6.

In this, 1 µg of the plasmid DNA pPT-DB1 that had been prepared in Example 6was subjected to PCR of two different types, using it as the template. Precisely, for PCR reaction No. 1, used was a reaction system of 50 µl in total, comprising 50 pmols of the primer having the sequence of Sequence Number 34 in Sequence Listing and 50 pmols of an M13 primer M4 (having the sequence of Sequence Number 10 in Sequence Listing) (for the composition of this system, referred to were themanufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 µl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 µl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 23, in which it is known that the 108th Glu in the β-subunit of the nitrile hydratase from the clone shown therein was substituted with Arg.

TABLE 23

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 23 | 108th position in β-subunit | Glu | Arg | GAG | CGG |

Example 29

The Mutant (24) with the Partial Substituted Amino Acid Sequence Having Nitrile Hydratase Activity:

This is to demonstrate the substitution with Cys for the 108th Glu in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 35 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 24, in which it is known that the 108th Glu in the β-subunit of the nitrile hydratase from the clone shown therein was substituted with Cys.

TABLE 24

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 24 | 108th position in β-subunit | Glu | Cys | GAG | TGC |

Example 30

The Mutant (25) with the Partial Substituted Amino Acid Sequence Having Nitrile Hydratase Activity:

This is to demonstrate the substitution with Leu for the 108th Glu in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50μl in total, comprising 50 pmols of the primer having the sequence of Sequence Number 36 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an *E. coli* bank was prepared in the same manner as in Example 6.

One platinum loop of any one of five clones as unlimitedly selected from the *E. coli* bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 25, in which it is known that the 108th Glu in the β-subunit of the nitrile hydratase from the clone shown therein was substituted with Leu.

TABLE 25

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 25 | 108th position in β-subunit | Glu | Leu | GAG | CTG |

Example 31

The Mutant (26) with the Partial Substituted Amino Acid Sequence Having Nitrile Hydratase Activity:

This is to demonstrate the substitution with Thr for the 108th Glu in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 37 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 26, in which it is known that the 108th Glu in the β-subunit of the nitrile hydratase from the clone shown therein was substituted with Thr.

TABLE 26

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 26 | 108th position in β-subunit | Glu | Thr | GAG | ACG |

Example 32

The Mutant (27) with the Partial Substituted Amino Acid Sequence Having Nitrile Hydratase Activity:

This is to demonstrate the substitution with Asp for the 200th Ala in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50 μl in total, comprising 50 pmols of the primer having the sequence of Sequence Number 38 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 27, in which it is known that the 200th Ala in the β-subunit of the nitrile hydratase from the clone shown therein was substituted with Asp.

TABLE 27

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 27 | 200th position in β-subunit | Ala | Asp | GCC | GAC |

Example 33

The Mutant (28) with the Partial Substituted Amino Acid Sequence Having Nitrile Hydratase Activity:

This is to demonstrate the substitution with Ile for the 200th Ala in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50 μl in total, comprising 50 pmols of the primer having the sequence of Sequence Number 39 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 28, in which it is known that the 200th Ala in the β-subunit of the nitrile hydratase from the clone shown therein was substituted with Ile.

TABLE 28

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 28 | 200th position in β-subunit | Ala | Ile | GCC | ATC |

Example 34

The Mutant (29) with the Partial Substituted Amino Acid Sequence Having Nitrile Hydratase Activity:

This is to demonstrate the substitution with Val for the 200th Ala in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50 μl in total, comprising 50 pmols of the primer having the sequence of Sequence Number 40 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 29, in which it is known that the 200th Ala in the β-subunit of the nitrile hydratase from the clone shown therein was substituted with Val.

TABLE 29

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 29 | 200th position in β-subunit | Ala | Val | GCC | GTC |

Example 35

The Mutant (30) with the Partial Substituted Amino Acid Sequence Having Nitrile Hydratase Activity:

This is to demonstrate the substitution with Glu for the 200th Ala in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6was subjected to PCR of two different types, using it as the template. Precisely, for PCR reaction No. 1, used was a reaction system of 50μl in total, comprising 50 pmols of the primer having the sequence of Sequence Number 41 in Sequence Listing and 50 pmols of an M13 primer M4 (having the sequence of Sequence Number 10 in Sequence Listing) (for the compositionof this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 30, in which it is known that the 200th Ala in the β-subunit of the nitrile hydratase from the clone shown therein was substituted with Glu.

TABLE 30

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 30 | 200th position in β-subunit | Ala | Glu | GCC | GAG |

Example 36

The Mutant (31) with the Partial Substituted Amino Acid Sequence Having Nitrile Hydratase Activity:

This is to demonstrate the substitution with Tyr for the 212nd Ser in the β-subunit region in the plasmid DNA pPT-DB1. Using it as the template, the plasmid DNA pPT-DB1 was subjected to site-specific mutation in the same manner as in Example 6.

In this, 1 μg of the plasmid DNA pPT-DB1 that had been prepared in Example 6 was subjected to PCR of two different types, using it as the template. Precisely, for PCR reaction No. 1, used was a reaction system of 50 μl in total, comprising 50 pmols of the primer having the sequence of Sequence Number 42 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 31, in which it is known that the 212nd Ser in the β-subunit of the nitrile hydratase from the clone shown therein was substituted with Tyr.

TABLE 31

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 31 | 212nd position in β-subunit | Ser | Tyr | TCC | TAC |

Example 37

The Mutant (32) with the Multi-Substituted Amino Acid Sequence Having Nitrile Hydratase Activity:

This is to demonstrate that the mutant with the multi-substituted amino acid sequence comprising both of the mutated position from the clone No. 5 (where the 19th Ala in the α-subunit was substituted with Val) and that from the clone No. 11 (where the 126th Phe in the α-subunit was substituted with Tyr) still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 11 that had been prepared in Example 16 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 11 through alkali SDS extraction.

One μg of the plasmid DNA of the clone No. 11 was subjected to PCR of two different types, using it as the template. Precisely, for PCR reaction No. 1, used was a reaction system of 50 μl in total, comprising 50 pmols of the primer having the sequence of Sequence Number 16 in Sequence Listing and 50 pmols of an M13 primer M4 (having the sequence of Sequence Number 10 in Sequence Listing) (for the composition of this system, referred to were the manufacturer's instructions for the kit) The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 32, in which it is known that, in the amino acid sequence of the plasmid DNA as prepared herein, the 19th Ala in the α-subunit in the wild nitrile hydratase was substituted with Val and the 126th Phe in the same was substituted with Tyr.

TABLE 32

| Clone Number | Mutated Sites (in α-subunit) | Change in Amino Acid Sequence | | Change in Base Sequence | |
|---|---|---|---|---|---|
| | | Wild Type | Mutant | Wild Type | Mutant |
| No. 32 | 19th position in α-subunit | Ala | Val | GCG | GTG |
| | 126th position in α-subunit | Phe | Tyr | TTC | TAC |

Example 38

The Mutant (33) with the Multi-Substituted Amino Acid Sequence Having Nitrile Hydratase Activity:

This is to demonstrate that the mutant with the multi-substituted amino acid sequence comprising both of the mutated position from the clone No. 1 (where the 6th Leu in the α-subunit was substituted with Met) and that from the clone No. 32 (where the 19th Ala in the α-subunit was substituted with Val and the 126th Phe in the α-subunit was substituted with Tyr) still had the nitrile hydratase activity.

49

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 32 that had been prepared in Example 37 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 32 through alkali SDS extraction.

One μg of the plasmid DNA of the clone No. 32 was subjected to PCR of two different types, using it as the template. Precisely, for PCR reaction No. 1, used was a reaction system of 50 μl in total, comprising 50 pmols of the primer having the sequence of Sequence Number 9 in Sequence Listing and 50 pmols of an M13 primer M4 (having the sequence of Sequence Number 10 in Sequence Listing) (for the composition of this system, referred to were the manufacturer's instructions for the kit) The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 33, in which it is known that, in the amino acid sequence of the plasmid DNA as prepared herein, the 6th Leu in the α-subunit in the wild nitrile hydratase was substituted with Met, the 19th Ala in the same was substituted with Val, and the 126th Phe in the same was substituted with Tyr.

50

TABLE 33

| Clone Number | Mutated Sites | Change in Amino Acid Sequence | | Change in Base Sequence | |
|---|---|---|---|---|---|
| | | Wild Type | Mutant | Wild Type | Mutant |
| No. 33 | 6th position in α-subunit | Leu | Met | CTG | ATG |
| | 19th position in α-subunit | Ala | Val | GCG | GTG |
| | 126th position in α-subunit | Phe | Tyr | TTC | TAC |

Example 39

The Mutant (34) with the Multi-Substituted Amino Acid Sequence Having Nitrile Hydratase Activity:

This is to demonstrate that the mutant with the multi-substituted amino acid sequence comprising both of the mutated position from the clone No. 2 (where the 6th Leu in the α-subunit was substituted with Thr) and that from the clone No. 32 (where the 19th Ala in the α-subunit was substituted with Val and the 126th Phe in the α-subunit was substituted with Tyr) still had the nitrile hydratase activity.

One μg of the plasmid DNA of the clone No. 32 that had been prepared in Example 38 was subjected to PCR of two different types, using it as the template. Precisely, for PCR reaction No. 1, used was a reaction system of 50 μl in total, comprising 50 pmols of the primer having the sequence of Sequence Number 13 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 34, in which it is known that, in the amino acid sequence of the plasmid DNA as prepared herein, the 6th Leu in the α-subunit in the wild nitrile hydratase was substituted with Thr, the 19th Ala in the same was substituted with Val, and the 126th Phe in the same was substituted with Tyr.

TABLE 34

| Clone | | Change in Amino Acid Sequence | | Change in Base Sequence | |
|---|---|---|---|---|---|
| Number | Mutated Sites | Wild Type | Mutant | Wild Type | Mutant |
| No. 34 | 6th position in α-subunit | Leu | Thr | CTG | ACG |
| | 19th position in α-subunit | Ala | Val | GCG | GTG |
| | 126th position in α-subunit | Phe | Tyr | TTC | TAC |

Example 40

The Mutant (35) with the Multi-Substituted Amino Acid Sequence Having Nitrile Hydratase Activity:

This is to demonstrate that the mutant with the multi-substituted amino acid sequence comprising both of the mutated position from the clone No. 3 (where the 6th Leu in the α-subunit was substituted with Ala) and that from the clone No. 32 (where the 19th Ala in the α-subunit was substituted with Val and the 126th Phe in the α-subunit was substituted with Tyr) still had the nitrile hydratase activity.

One μg of the plasmid DNA of the clone No. 32 that had been prepared in Example 38 was subjected to PCR of two different types, using it as the template. Precisely, for PCR reaction No. 1, used was a reaction system of 50 μl in total, comprising 50 pmols of the primer having the sequence of Sequence Number 14 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 35, in which it is known that, in the amino acid sequence of the plasmid DNA as prepared herein, the 6th Leu in the α-subunit in the wild nitrile hydratase was substituted with Ala, the 19th Ala in the same was substituted with Val, and the 126th Phe in the same was substituted with Tyr.

TABLE 35

| Clone | | Change in Amino Acid Sequence | | Change in Base Sequence | |
|---|---|---|---|---|---|
| Number | Mutated Sites | Wild Type | Mutant | Wild Type | Mutant |
| No. 35 | 6th position in α-subunit | Leu | Ala | CTG | GCG |
| | 19th position in α-subunit | Ala | Val | GCG | GTG |
| | 126th position in α-subunit | Phe | Tyr | TTC | TAC |

Example 41

The Mutant (36) with the Multi-Substituted Amino Acid Sequence Having Nitrile Hydratase Activity:

This is to demonstrate that the mutant with the multi-substituted amino acid sequence comprising both of the mutated position from the clone No. 20 (where the 108th Glu in the β-subunit was substituted with Asp) and that from the clone No. 31 (where the 212nd Ser in the β-subunit was substituted with Tyr) still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 31 that had been prepared in Example 36 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 31 through alkali SDS extraction.

One μg of the plasmid DNA of the clone No. 31 was subjected to PCR of two different types, using it as the template. Precisely, for PCR reaction No. 1, used was a reaction system of 50 μl in total, comprising 50 pmols of the primer having the sequence of Sequence Number 31 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 36, in which it is known that, in the amino acid sequence of the plasmid DNA as prepared herein, the 108th Glu in the β-subunit in the wild nitrile hydratase was substituted with Asp and the 212nd Ser in the same was substituted with Tyr.

TABLE 36

| Clone | | Change in Amino Acid Sequence | | Change in Base Sequence | |
|---|---|---|---|---|---|
| Number | Mutated Sites | Wild Type | Mutant | Wild Type | Mutant |
| No. 36 | 108th position in β-subunit | Glu | Asp | GAG | GAT |
| | 212nd position in β-subunit | Ser | Tyr | TCC | TAC |

Example 42

The Mutant (37) with the Multi-Substituted Amino Acid Sequence Having Nitrile Hydratase Activity:

This is to demonstrate that the mutant with the multi-substituted amino acid sequence comprising both of the mutated position from the clone No. 23 (where the 108th Glu in the β-subunit was substituted with Arg) and that from the clone No. 31 (where the 212nd Ser in the β-subunit was substituted with Tyr) still had the nitrile hydratase activity.

One μg of the plasmid DNA of the clone No. 31 that had benn prepared in the Example 41 was subjected to PCR of two different types, using it as the template. Precisely, for PCR reaction No. 1, used was a reaction system of 50 μl in total, comprising 50 pmols of the primer having the sequence of Sequence Number 34 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 37, in which it is known that, in the amino acid sequence of the plasmid DNA as prepared herein, the 108th Glu in the β-subunit in the wild nitrile hydratase was substituted with Arg and the 212nd Ser in the same was substituted with Tyr.

TABLE 37

| Clone | | Change in Amino Acid Sequence | | Change in Base Sequence | |
|---|---|---|---|---|---|
| Number | Mutated Sites | Wild Type | Mutant | Wild Type | Mutant |
| No. 37 | 108th position in β-subunit | Glu | Arg | GAG | CGG |
| | 212nd position in β-subunit | Ser | Tyr | TCC | TAC |

Example 43

The Mutant (38) with the Multi-Substituted Amino Acid Sequence Having Nitrile Hydratase Activity:

This is to demonstrate that the mutant with the multi-substituted amino acid sequence comprising both of the mutated position from the clone No. 27 (where the 200th Ala in the β-subunit was substituted with Asp) and that from the clone No. 31 (where the 212nd Ser in the β-subunit was substituted with Tyr) still had the nitrile hydratase activity.

One μg of the plasmid DNA of the clone No. 31 that had benn prepared in the Example 41 was subjected to PCR of two different types, using it as the template. Precisely, for PCR reaction No. 1, used was a reaction system of 50 μl in total, comprising 50 pmols of the primer having the sequence of Sequence Number 38 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as on Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culturewas put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 38, in which it is known that, in the amino acid sequence of the plasmid DNA as prepared herein, the 200th Ala in the β-subunit in the wild nitrile hydratase was substituted with Asp and the 212nd Ser in the same was substituted with Tyr.

TABLE 38

| Clone | | Change in Amino Acid Sequence | | Change in Base Sequence | |
| --- | --- | --- | --- | --- | --- |
| Number | Mutated Sites | Wild Type | Mutant | Wild Type | Mutant |
| No. 38 | 200th position in β-subunit | Ala | Asp | GCC | GAC |
| | 212nd position in β-subunit | Ser | Tyr | TCC | TAC |

Example 44

The Mutant (39) with the Multi-Substituted Amino Acid Sequence Having Nitrile Hydratase Activity:

This is to demonstrate that the mutant with the multi-substituted amino acid sequence comprising both of the mutated position from the clone No. 30 (where the 200th Ala in the β-subunit was substituted with Glu) and that from the clone No. 31 (where the 212nd Ser in the β-subunit was substituted with Tyr) still had the nitrile hydratase activity.

One μg of the plasmid DNA of the clone No. 31 that had benn prepared in the Example 41 was subjected to PCR of two different types, using it as the template. Precisely, for PCR reaction No. 1, used was a reaction system of 50 μl in total, comprising 50 pmols of the primer having the sequence of Sequence Number 41 in Sequence Listing and 50 pmols of an M13 primer M4 (having the sequence of Sequence Number 10 in Sequence Listing) (for the composition of this system, referred to were the manufacturer's instructions for the kit). The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 39, in which it is known that, in the amino acid sequence of the plasmid DNA as prepared herein, the 200th Ala in the β-subunit in the wild nitrile hydratase was substituted with Glu and the 212nd Ser in the same was substituted with Tyr.

TABLE 39

| Clone Number | Mutated Sites | Change in Amino Acid Sequence | | Change in Base Sequence | |
|---|---|---|---|---|---|
| | | Wild Type | Mutant | Wild Type | Mutant |
| No. 39 | 200th position in β-subunit | Ala | Glu | GCC | GAG |
| | 212nd position in β-subunit | Ser | Tyr | TCC | TAC |

Example 45

The Mutant (40) with the Multi-Substituted Amino Acid Sequence Having Nitrile Hydratase Activity:

This is to demonstrate that the mutant with the multi-substituted amino acid sequence comprising both of the mutated position from the clone No. 23 (where the 108th Glu in the β-subunit was substituted with Arg) and that from the clone No. 39 (where the 200nd Ala in the β-subunit was substituted with Glu and the 212nd Ser in the same was substituted with Tyr) still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 39 that had been prepared in Example 44 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 39 through alkali SDS extraction.

One μg of the plasmid DNA of the clone No. 39 was subjected to PCR of two different types, using it as the template. Precisely, for PCR reaction No. 1, used was a reaction system of 50 μl in total, comprising 50 pmols of the primer having the sequence of Sequence Number 34 in Sequence Listing and 50 pmols of an M13 primer M4 (having the sequence of Sequence Number 10 in Sequence Listing) (for the composition of this system, referred to were the manufacturer's instructions for the kit) The reaction No. 1 was comprised of 25 PCR cycles, in which one PCR cycle comprised thermal denaturation at 98° C. for 15 seconds, annealing at 55° C. for 30 seconds and chain extension at 72° C. for 120 seconds. For PCR reaction No. 2, used was a reaction system of 50 μl in total, comprising 50 pmols of an MUT 4 primer (having the sequence of Sequence Number 11 in Sequence Listing) and 50 pmols of an M13 primer RV (having the sequence of Sequence Number 12 in Sequence Listing) (for the composition of this system, referred to were the manufacturer's instructions for the kit). The reaction No. 2 was comprised of 25 PCR cycles, in which one PCR cycle was the same as that in the reaction No. 1. After PCR, 5 μl of the reaction mixture obtained in each of the reaction Nos. 1 and 2 was subjected to agarose gel electrophoresis (where the agarose concentration was 1.0% by weight), thereby detecting, if any, the product resulting from the amplification of the DNA in the reaction mixture. This detection revealed the production of the amplified DNA products in the both PCR reactions. Using these products, an E. coli bank was prepared in the same manner as in Example 6.

One platinum loop of any one of five clones as unlimitedly selected from the E. coli bank was inoculated on 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was measured in the same manner as in Example 6. As a result, the formation of acrylamide was detected in four of the five clones, which verifies that the four clones had a nitrile hydratase activity.

From one ml of each of the cultures of the active four clones, which had remained herein without being used for the detection of the nitrile hydratase activity thereof, the cells were separated and subjected to alkali SDS extraction to thereby extract the plasmid DNA of each clone. Next, the base sequence of the nitrile hydratase structural gene of each clone was sequenced in the same manner as in Example 2. The results are shown in Table 40, in which it is known that, in the amino acid sequence of the plasmid DNA as prepared herein, the 108th Glu in the β-subunit in the wild nitrile hydratase was substituted with Arg, the 200th Ala in the same was substituted with Glu, and the 212nd Ser in the same was substituted with Tyr.

TABLE 40

| Clone Number | Mutated Sites | Change in Amino Acid Sequence | | Change in Base Sequence | |
|---|---|---|---|---|---|
| | | Wild Type | Mutant | Wild Type | Mutant |
| No. 40 | 108th position in β-subunit | Glu | Arg | GAG | CGG |
| | 200th position in β-subunit | Ala | Glu | GCC | GAG |
| | 212nd position in β-subunit | Ser | Tyr | TCC | TAC |

Example 46

The Mutant (41) with the multi-substituted Amino Acid Sequence Having Nitrile Hydratase Activity:

This is to demonstrate that the mutant with the multi-substituted amino acid sequence comprising of the mutated position from the clone No. 34 and that from the clone No. 36 still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. Two same media of that type were prepared herein. One platinum loop of the clone No. 34 that had been prepared in Example 39 and one platinum loop of the clone No. 36 that had been prepared in Example 41 were separately inoculated on these media, and incubated therein at 37 ° C. for about 20 hours with stirring at 300 rpm. The resulting cultures of one ml each were separately put into suitable centrifugal tubes, and centrifuged at 15,000 rpm for 5 minutes to separate the cells from the cultures. From the respective cells were extracted the plasmid DNA of the clone No. 34 and the plasmid DNA of the clone No. 36 through alkali SDS extraction.

The plasmid DNA from the clone No. 36 was cleaved with restriction endonucleases EcoRI and NotI at the cleaving sites thereof, and then subjected to agarose gel electrophoresis (using a low-melting-point agarose, Sigma's Type VII, at an agarose concentration of 1.0%), through which the DNA fragment of about 770 bp was cut out of the agarose gel. In the same manner, the plasmid DNA from the clone No.34 was cleaved with restriction endonucleases EcoRI and NotI at the cleaving sites thereof, and then subjected to agarose gel electrophoresis (using a low-melting-point agarose, Sigma's Type VII, at an agarose concentration of 0.7%), through which the DNA fragment of about 3.8 Kbp was cut out of the agarose gel. Both the thus-cut agarose fragments (about 0.1 g each) were finely pulverized, then separately suspended in 1 ml of TE, and heated at 55° C. for 1 hour, whereby the fragments were completely melted. The resulting melts were separately subjected to the same phenol/chloroform extraction and ethanol precipitation as in Example 2, through which the fragments were purified. Finally, these were separately dissolved in 10 μl of TE.

The DNA fragment of about 770 bp obtained from the clone No. 36 and the DNA fragment of about 3.8 Kbp obtained from the clone No. 34 were ligated together, using a Takara Shuzo's DNA ligation kit, to construct a plasmid pPT-DB41. This plasmid DNA pPT-DB41 was introduced into competent cells of Escherichia coli HB101 (produced by Toyobo). Thus was obtained an E. coli clone No. 41.

One platinum loop of the cells of the E. coli clone No. 41 were inoculated onto 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was determined in the same manner as in Example 6. As a result, the formation of acrylamide was detected, which verifies that the clone No. 41 still had the nitrile hydratase activity.

From one ml of the culture, which had remained herein without being used for the detection of the nitrile hydratase activity thereof, the cells were separated and subjected to alkali SDS extraction to thereby extract the plasmid DNA of the clone. Next, the base sequence of the nitrile hydratase structural gene of the clone No. 41 was sequenced in the same manner as in Example 2. The results are shown in Table 41, in which it is known that, in the amino acid sequence of the plasmid DNA as prepared herein, the 6th Leu in the α-subunit in the wild nitrile hydratase was substituted with Thr, the 19th Ala in the same was substituted with Val, the 126th Phe in the same was substituted with Tyr, while the 108th Glu in the β-subunit in the wild nitrile hydratase was substituted with Asp, and the 212nd Ser in the same was substituted with Tyr.

TABLE 41

| Clone | | Change in Amino Acid Sequence | | Change in Base Sequence | |
|---|---|---|---|---|---|
| Number | Mutated Sites | Wild Type | Mutant | Wild Type | Mutant |
| No. 41 | 6th position in α-subunit | Leu | Thr | CTG | ACG |
| | 19th position in α-subunit | Ala | Val | GCG | GTG |
| | 126th position in α-subunit | Phe | Tyr | TTC | TAC |
| | 108th position in β-subunit | Glu | Asp | GAG | GAT |
| | 212nd position in β-subunit | Ser | Tyr | TCC | TAC |

Example 47

The Mutant (42) with the multi-substituted Amino Acid Sequence Having Nitrile Hydratase Activity:

This is to demonstrate that the mutant with the multi-substituted amino acid sequence comprising bot of the mutated position from the clone No. 34 and that from the clone No. 37 still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 37 that had been prepared in Example 42 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 37 through alkali SDS extraction.

The plasmid DNA from the clone No. 37 was cleaved with restriction endonucleases EcoRI and NotI at the cleaving sites thereof, and then subjected to agarose gel electrophoresis (using a low-melting-point agarose, Sigma's Type VII, at an agarose concentration of 1.0%), through which the DNA fragment of about 770 bp was cut out of the agarose gel. In the same manner, the plasmid DNA from the clone No.34 that had been prepared in the Example 46 was cleaved with restriction endonucleases EcoRI and NotI at the cleaving sites thereof, and then subjected to agarose gel electrophoresis (using a low-melting-point agarose, Signals Type VII, at an agarose concentration of 0.7%), through which the DNA fragment of about 3.8 Kbp was cut out of the agarose gel. Both the thus-cut agarose fragments (about 0.1 g each) were finely pulverized, then separately suspended in 1 ml of TE, and heated at 55° C. for 1 hour, whereby the fragments were completely melted. The resulting melts were separately subjected to the same phenol/chloroform extraction and ethanol precipitation as in Example 2, through which the fragments were purified. Finally, these were separately dissolved in 10 μl of TE.

The DNA fragment of about 770 bp obtained from the clone No. 37 and the DNA fragment of about 3.8 Kbp obtained from the clone No. 34 were ligated together, using a Takara Shuzo's DNA ligation kit, to construct a plasmid pPT-DB42. This plasmid DNA pPT-DB42 was introduced into competent cells of Escherichia coli HB101 (produced by Toyobo). Thus was obtained an E. coli clone No. 42.

One platinum loop of the cells of the E. coli clone No. 42 were inoculated onto 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was determined in the same manner as in Example 6. As a result, the formation of acrylamide was detected, which verifies that the clone No. 42 still had the nitrile hydratase activity.

From one ml of the culture, which had remained herein without being used for the detection of the nitrile hydratase activity thereof, the cells were separated and subjected to alkali SDS extraction to thereby extract the plasmid DNA of the clone. Next, the base sequence of the nitrile hydratase structural gene of the clone No. 42 was sequenced in the same manner as in Example 2. The results are shown in Table 42, in which it is known that, in the amino acid sequence of the plasmid DNA as prepared herein, the 6th Leu in the α-subunit in the wild nitrile hydratase was substituted with Thr, the 19th Ala in the same was substituted with Val, the 126th Phe in the same was substituted with Tyr, while the 108th Glu in the β-subunit in the wild nitrile hydratase was substituted with Arg, and the 212nd Ser in the same was substituted with Tyr.

TABLE 42

| Clone Number | Mutated Sites | Change in Amino Acid Sequence | | Change in Base Sequence | |
|---|---|---|---|---|---|
| | | Wild Type | Mutant | Wild Type | Mutant |
| No. 42 | 6th position in α-subunit | Leu | Thr | CTG | ACG |
| | 19th position in α-subunit | Ala | Val | GCG | GTG |
| | 126th position in α-subunit | Phe | Tyr | TTC | TAC |
| | 108th position in β-subunit | Glu | Arg | GAG | CGG |
| | 212nd position in β-subunit | Ser | Tyr | TCC | TAC |

Example 48

The Mutant (43) with the multi-substituted Amino Acid Sequence Having Nitrile Hydratase Activity:

This is to demonstrate that the mutant with the multi-substituted amino acid sequence comprising bot of the mutated position from the clone No. 34 and that from the clone No. 39 still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 39 that had been prepared in Example 44 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 39 through alkali SDS extraction.

The plasmid DNA from the clone No. 39 was cleaved with restriction endonucleases EcoRI and NotI at the cleaving sites thereof, and then subjected to agarose gel electrophoresis (using a low-melting-point agarose, Sigma's Type VII, at an agarose concentration of 1.0%), through which the DNA fragment of about 770 bp was cut out of the agarose gel. In the same manner, the plasmid DNA from the clone No.34 that had been prepared in the Example 46 was cleaved with restriction endonucleases EcoRI and NotI at the cleaving sites thereof, and then subjected to agarose gel electrophoresis (using a low-melting-point agarose, Sigmals Type VII, at an agarose concentration of 0.7%), through which the DNA fragment of about 3.8 Kbp was cut out of the agarose gel. Both the thus-cut agarose fragments (about 0.1 g each) were finely pulverized, then separately suspended in 1 ml of TE, and heated at 55° C. for 1 hour, whereby the fragments were completely melted. The resulting melts were separately subjected to the same phenol/chloroform extraction and ethanol precipitation as in Example 2, through which the fragments were purified. Finally, these were separately dissolved in 10 μl of TE.

The DNA fragment of about 770 bp obtained from the clone No. 39 and the DNA fragment of about 3.8 Kbp obtained from the clone No. 34 were ligated together, using a Takara Shuzo's DNA ligation kit, to construct a plasmid pPT-DB43. This plasmid DNA pPT-DB43 was introduced into competent cells of *Escherichia coli* HB101 (produced by Toyobo). Thus was obtained an *E. coli* clone No. 43.

One platinum loop of the cells of the *E. coli* clone No. 43 were inoculated onto 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was determined in the same manner as in Example 6. As a result, the formation of acrylamide was detected, which verifies that the clone No. 43 still had the nitrile hydratase activity.

From one ml of the culture, which had remained herein without being used for the detection of the nitrile hydratase activity thereof, the cells were separated and subjected to alkali SDS extraction to thereby extract the plasmid DNA of the clone. Next, the base sequence of the nitrile hydratase structural gene of the clone No. 43 was sequenced in the same manner as in Example 2. The results are shown in Table 43, in which it is known that, in the amino acid sequence of the plasmid DNA as prepared herein, the 6th Leu in the α-subunit in the wild nitrile hydratase was substituted with Thr, the 19th Ala in the same was substituted with Val, the 126th Phe in the same was substituted with Tyr, while the 200th Ala in the β-subunit in the wild nitrile hydratase was substituted with Glu, and the 212nd Ser in the same was substituted with Tyr.

TABLE 43

| Clone Number | Mutated Sites | Change in Amino Acid Sequence | | Change in Base Sequence | |
|---|---|---|---|---|---|
| | | Wild Type | Mutant | Wild Type | Mutant |
| No. 43 | 6th position in α-subunit | Leu | Thr | CTG | ACG |
| | 19th position in α-subunit | Ala | Val | GCG | GTG |
| | 126th position in α-subunit | Phe | Tyr | TTC | TAC |
| | 200th position in β-subunit | Ala | Glu | GCC | GAG |
| | 212nd position in β-subunit | Ser | Tyr | TCC | TAC |

Example 49

The Mutant (44) with the multi-substituted Amino Acid Sequence Having Nitrile Hydratase Activity:

This is to demonstrate that the mutant with the multi-substituted amino acid sequence comprising bot of the mutated position from the clone No. 34 and that from the clone No. 40 still had the nitrile hydratase activity.

10 ml of a liquid LB medium was put into a 30-ml test tube, and sterilized by autoclaving at 121° C. for 20 minutes. To this medium, added was ampicillin to have a final concentration of 100 μg/ml. One platinum loop of the clone No. 40 that had been prepared in Example 45 was inoculated on the medium, and incubated therein at 37° C. for about 20 hours with stirring at 300 rpm. One ml of the resulting culture was put into a suitable centrifugal tube, and centrifuged at 15,000 rpm for 5 minutes to separate the cells from the culture. From the cells was extracted the plasmid DNA of the clone No. 40 through alkali SDS extraction.

The plasmid DNA from the clone No. 40 was cleaved with restriction endonucleases EcoRI and NotI at the cleaving sites thereof, and then subjected to agarose gel electrophoresis (using a low-melting-point agarose, Sigma's Type VII, at an agarose concentration of 1.0%), through which the DNA fragment of about 770 bp was cut out of the agarose gel. In the same manner, the plasmid DNA from the clone No.34 that had been prepared in the Example 46 was cleaved with restriction endonucleases EcoRI and NotI at the cleaving sites thereof, and then subjected to agarose gel electrophoresis (using a low-melting-point agarose, Sigma's Type VII, at an agarose concentration of 0 7%), through which the DNA fragment of about 3.8 Kbp was cut out of the agarose gel. Both the thus-cut agarose fragments (about 0.1 g each) were finely pulverized, then separately suspended in 1 ml of TE, and heated at 55° C. for 1 hour, whereby the fragments were completely melted. The resulting melts were separately subjected to the same phenol/chloroform extraction and ethanol precipitation as in Example 2, through which the fragments were purified. Finally, these were separately dissolved in 10 μl of TE.

The DNA fragment of about 770 bp obtained from the clone No. 40 and the DNA fragment of about 3.8 Kbp obtained from the clone No. 34 were ligated together, using a Takara Shuzo's DNA ligation kit, to construct a plasmid pPT-DB44. This plasmid DNA pPT-DB44 was introduced into competent cells of *Escherichia coli* HB101 (produced by Toyobo). Thus was obtained an *E. coli* clone No. 44.

One platinum loop of the cells of the *E. coli* clone No. 44 were inoculated onto 10 ml of the same activity expression medium as that used in Example 6, and incubated therein at 37° C. for about 20 hours with stirring at 300 rpm. One ml of the resulting culture was put into a suitable centrifugal tube, and its nitrile hydratase activity was determined in the same manner as in Example 6. As a result, the formation of acrylamide was detected, which verifies that the clone No. 44 still had the nitrile hydratase activity.

From one ml of the culture, which had remained herein without being used for the detection of the nitrile hydratase activity thereof, the cells were separated and subjected to alkali SDS extraction to thereby extract the plasmid DNA of the clone. Next, the base sequence of the nitrile hydratase structural gene of the clone No. 44 was sequenced in the same manner as in Example 2. The results are shown in Table 44, in which it is known that, in the amino acid sequence of the plasmid DNA as prepared herein, the 6th Leu in the α-subunit in the wild nitrile hydratase was substituted with Thr, the 19th Ala in the same was substituted with Val, the 126th Phe in the same was substituted with Tyr, while the 108th Glu in the β-subunit in the wild nitrile hydratase was substituted with Arg, the 200th Ala in the same was substituted with Glu, and the 212nd Ser in the same was substituted with Tyr.

TABLE 44

| Clone | | Change in Amino Acid Sequence | | Change in Base Sequence | |
|---|---|---|---|---|---|
| Number | Mutated Sites | Wild Type | Mutant | Wild Type | Mutant |
| No. 44 | 6th position in α-subunit | Leu | Thr | CTG | ACG |
| | 19th position in α-subunit | Ala | Val | GCG | GTG |
| | 126th position in α-subunit | Phe | Tyr | TTC | TAC |
| | 108th position in β-subunit | Glu | Arg | GAG | CGG |
| | 200th position in β-subunit | Ala | Glu | GCC | GAG |
| | 212nd position in β-subunit | Ser | Tyr | TCC | TAC |

ADVANTAGES OF THE INVENTION

According to the present invention, there is provided the amino acid sequence and base sequence of a *Pseudonocardia thermophila*-derived nitrile hydratase. Also provided are a method for changing its amino acid sequence and base sequence without substantially changing the functions of said nitrile hydratase, and nitrile hydratases having a base sequence and an amino acid sequence as changed on the basis of said method. Further provided are a recombinant plasmid having the gene of said nitrile hydratase, a transformant containing said recombinant plasmid, a method of using said transformant for producing said enzyme, and a method of using said transformant for producing the corresponding amide compound from a nitrile compound.

---

What is claimed is:

1. A nitrile hydratase which comprises an α-subunit having the amino acid sequence of SEQ ID NO: 1 and a β-subunit having the amino acid sequence of SEQ ID NO: 2.

2. The nitrile hydratase as claimed in claim 1, which is derived from *Pseudonocardia thermophila*.

3. A nitrile hydratase which comprises, as the constitute element, an α-subunit to be derived from the amino acid sequence of SEQ ID NO: 1 through substitution of one or more amino acids of the 6th, 19th, 38th, 77th, 90th, 102nd, 106th, 126th, 130th, 142nd, 146th, 187th, 194th and 203rd amino acids in said sequence with any other amino acid(s).

4. A nitrile hydratase which comprises, as the constitute element, a β-subunit to be derived from the amino acid sequence of SEQ ID NO: 2 through substitution of one or more amino acids of the 20th, 21st, 108th, 200th and 212nd amino acids in said sequence with any other amino acid (s).

* * * * *